(12) United States Patent
Zhu et al.

(10) Patent No.: US 12,024,732 B2
(45) Date of Patent: Jul. 2, 2024

(54) METHOD FOR PREPARING NITROGEN-CONTAINING HETEROCYCLIC COMPOUND AND DERIVATIVE THEREOF BY ENZYMATIC-CHEMICAL CASCADE METHOD

(71) Applicant: NANJING TECH UNIVERSITY, Nanjing (CN)

(72) Inventors: Chenjie Zhu, Nanjing (CN); Hanjie Ying, Nanjing (CN); Zhuotao Tan, Nanjing (CN); Wei Zhuang, Nanjing (CN); Yaping Fu, Nanjing (CN); Yaoying Han, Nanjing (CN); Ming Li, Nanjing (CN); Yong Chen, Nanjing (CN); Dong Liu, Nanjing (CN); Huanqing Niu, Nanjing (CN); Pengpeng Yang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 18/253,861

(22) PCT Filed: Aug. 18, 2021

(86) PCT No.: PCT/CN2021/113184
§ 371 (c)(1),
(2) Date: May 22, 2023

(87) PCT Pub. No.: WO2022/110916
PCT Pub. Date: Jun. 2, 2022

(65) Prior Publication Data
US 2024/0026400 A1 Jan. 25, 2024

(30) Foreign Application Priority Data
Nov. 27, 2020 (CN) .......................... 202011362322.2

(51) Int. Cl.
C12P 17/16 (2006.01)
C12N 9/04 (2006.01)
(Continued)

(52) U.S. Cl.
CPC ............ *C12P 17/16* (2013.01); *C12N 9/0006* (2013.01); *C12P 17/12* (2013.01); *C12P 17/14* (2013.01);
(Continued)

(58) Field of Classification Search
None
See application file for complete search history.

(56) References Cited

U.S. PATENT DOCUMENTS

2017/0114085 A1* 4/2017 Ying .................... C07H 19/207

FOREIGN PATENT DOCUMENTS

| CN | 105622693 | 6/2016 |
| CN | 108823258 | 11/2018 |

OTHER PUBLICATIONS

Zhu ("Nonenzymatic and Metal-Free Organocatalysis of in Situ Regeneration of Oxidized CoFactors by Activation and Reduction of Molecular Oxygen" ACS Catalysis, 2016, 6, 4989-4994), (Year: 2016).*

(Continued)

*Primary Examiner* — Robert J Yamasaki
*Assistant Examiner* — Charles Zoltan Constantine
(74) *Attorney, Agent, or Firm* — CBM PATENT CONSULTING, LLC

(57) ABSTRACT

A method for preparing a nitrogen-containing heterocyclic compound and a derivative thereof by an enzymatic-chemical cascade method, comprising: reacting an alcohol, an amine, an alcohol dehydrogenase, a flavin molecule and a coenzyme in a solvent to obtain the nitrogen-containing heterocyclic compound and the derivative thereof; compared with the prior art, the method is a green and economical enzymatic-chemical cascade method, and is used for synthesizing nitrogen-containing heterocyclic compounds and derivatives thereof; compared with a common toxic chemical catalyst, the alcohol dehydrogenase is selected as a catalyst in the method, which has the characteristics of high substrate specificity, no pollution, high catalytic efficiency, no toxic solvents and simple post-treatment.

5 Claims, 17 Drawing Sheets

(51) Int. Cl.
*C12P 17/12* (2006.01)
*C12P 17/14* (2006.01)
(52) U.S. Cl.
CPC ............. *C12Y 101/01001* (2013.01); *C12Y 101/01255* (2013.01)

(56) References Cited

OTHER PUBLICATIONS

Alexander T. Murray, et al. Biomimetic Flavin-Catalyzed Aldehyde Oxidation Organic Letters vol. 14, Issue 14 pp. 3656-3659 Publication date: 2012-12-32-1.

Alexander T. Murray, et al. Catalytic Amine Oxidation under AmbientAerobic Conditions :Mimicry ofMonoamine Oxidase B Angew. Chem. Int. Ed. No. 54 pp. 8997-9000 Publication date: Dec. 31, 2015.

Zhu Chenjie et al Research progress of natural nicotinamide cofactor regeneration system and its artificial analogues Journal of chemical industry and engineeringvol. 69, Issue 1, pp. 259-271 Publication date: Dec. 31, 2018.

\* cited by examiner

METHOD FOR PREPARING NITROGEN-CONTAINING HETEROCYCLIC COMPOUND AND DERIVATIVE THEREOF BY ENZYMATIC-CHEMICAL CASCADE METHOD

TECHNICAL FIELD

The present invention belongs to the field of biochemical engineering, and particularly relates to a novel method for preparing a nitrogen-containing heterocyclic compound and a derivative thereof by an enzymatic-chemical cascade method.

BACKGROUND

A nitrogen-containing heterocyclic compound and a derivative thereof are important members of a heterocyclic compound family, and widely exist in natural products and drug molecules. These compounds show wide biological and pharmacological activities, and play a vital role in many fields such as biology, medicines and materials. Focusing on the research of a novel method for a nitrogen-containing heterocyclic compound and a derivative thereof, we have constructed a new green method for synthesizing different nitrogen-containing heterocyclic compounds and derivatives thereof by chemoenzymatic cascade catalysis, comprising five-membered (pyrrole, pyrrolidone, pyrazole, imidazole, etc.), six-membered (pyridine, pyrazine, etc.), fused (indole, benzimidazole, etc.) and other nitrogen-containing heterocyclic compounds and derivatives thereof.

A pyrrole-containing N-heterocyclic ring is an important structural motif, and is widely used in drugs, pesticides, catalysts, functional materials and supramolecular chemistry. Many new synthetic methods have been developed to construct this type of drug intermediate, such as metal-catalyzed cyclization, cycloaddition, rearrangement, multi-component oxidative coupling, and hydroamination/cyclization. An N-substituted pyrrole is synthesized with a primary amine through Paal-Knorr condensation from a 1,4-dicarbonyl compound in the existence of a metal catalyst under an acidic condition, a developed cobalt-nitrogen catalyst can tolerate an acidic liquid hydrogen donor (HCOOH), which may be attributed to highly dispersed metal particles, and these particles are coordinated and stabilized by nitrogen species of solid carbonaceous carriers. This unique heterogeneous feature of a non-noble metal catalyst can not only significantly reduce a loss of a metal type and an overall production cost during reaction, but also provide the use of sustainable HCOOH instead of combustible hydrogen as a $H^+$ supplier. The non-catalytic dehydrogenation coupling of 1,4-butanediol or 1,4-substituted 1,4-butanediol and amine is carried out on a non-noble metal complex (such as a pliers complex of cobalt or manganese), and although these homogeneous catalytic systems show an excellent performance in Paal-Knorr condensation reaction, the difficulty of catalyst recovery will lead to an additional cost and a negative impact on environment. Michlik and Kempe reported that a 2,5-disubstituted pyrrole was synthesized from sustainable secondary alcohol and amino alcohol by continuous dehydrogenation in the existence of sodium tert-butoxide and an organic iridium catalyst. Another method for synthesizing the pyrrole is that catalytic amination is carried out on a biologically derived furan compound with the primary amine in the existence of an acid catalyst (such as $Al_2O_3$ and $TiO_2$), and a yield of the pyrrole derivative is increased by 20% to 60%. Li, et al. developed a general strategy without needing a catalyst or external hydrogen, which involved in-situ controlled release of HCOOH with $H_2O$ from an N-formyl substance (such as $HCONH_2$) for cyclization of amine and other ketoacids. A reaction system without a catalyst seems to be more sustainable and economical for the production of pyrrolidone, but a reaction rate of the reaction system is much lower than that of metal or acid catalysis.

Pyridine is a six-membered heterocyclic compound with a conjugated structure, the pyridine and a derivative thereof are widely used in the synthesis of pesticides, medicines and natural products, such as an antibiotics Cefalexin, an anti-ulcer drug Omeprazole and an antihypertensive drug Pinacidil, a pyridine ring and a benzene ring are bioelectronic isotopes, when the pyridine ring replaces the benzene ring, the compound activity is obviously improved, and the toxicity is greatly reduced, and this type of nitrogen-containing heterocyclic compound has a wide application range, and has attracted extensive attention from scholars at home and abroad, with rapidly developed industrial production and scientific research. At present, many methods for constructing a pyridine substitute have been reported, and traditionally, the pyridine is mainly synthesized by the condensation of amine and carbonyl compound, comprising the condensation of 1,5-dicarbonyl and amine, the (2+2+1+1) condensation of Hantzsch pyridine, and the (3+3) cyclization of 1,3-dicarbonyl derivatives with intercalated acrylamide. Although some synthetic methods are efficient, the application of the methods in constructing some practical but sensitive pyridine derivatives is directly limited due to an unstable precursor, an expensive metal catalyst, environmental pollution and complicated operation. Therefore, a flexible, efficient and green synthetic method is worth being expected.

A benzimidazole compound has special structure, physiological activity and reactivity, and important biological activity, and is an important bioactive molecule in the field of medicines, and the benzimidazole and a derivative thereof are an important component in pharmaceutical industry. The benzimidazole compound has the functions of blood lipid regulation, blood pressure lowering, cancer resistance, anti-convulsion, pain relief, calming, inflammation diminishing, immune system regulation, oxidation inhibition, blood coagulation inhibition, diabetes resistance, hormone level regulation and central nervous system excitement regulation, and also has the effects of microorganism resistance, virus and parasite killing, ulcer prevention and fungus killing. Therefore, the benzimidazole compound is widely used, and the research on the synthesis and application of the benzimidazole and the derivative thereof has never been stopped for decades, and is still very active up to now. With the continuous development of the research on the application of the benzimidazole compound, the related research on the synthesis of the benzimidazole compound has also attracted extensive attention of researchers. People try to give up harsh reaction conditions such as traditional strong acid catalysis and high temperature reaction, and in order to meet the requirement of "green chemistry", researchers are constantly striving to develop more efficient and environmentally friendly new synthetic methods. There are two general methods for synthesizing the benzimidazole compound, wherein one method refers to coupling of a carboxylic acid or a derivative thereof (nitrile, imidoate or orthoester) with phenylenediamine, and the coupling is usually carried out under strong acidic and harsh dehydrated condition (usually requiring high temperature) or by using a reagent such as phosphoric anhydride. The other method refers to oxidative dehydrogenation of an aniline Schiff base, which is usually produced in situ by a condensation reaction of phenylenediamine and aldehyde, with agents such as $MnO_2$, $Pb(OAc)_4$, $PhI(OAc)_2$, potassium monopersulfate, 2,3-dichloro-5,6-dicyanobenzoquinone (DDQ), $I_2$, 1,4-benzoquinone, tetracyanoethylene, benzofuran, $NaHSO_3$, $Na_2S_2O_5$, $(NH_4)_2S_2O_8$ and DMF (high-boiling-point oxidant/solvent) used as oxidants to execute the dehydrogenation steps. Although the above two methods are practical, there are still corresponding problems, such as the use of dangerous or toxic reagents, or the formation of N-benzyl benzimidazole by-products during dehydrogenation of an oxidation ring of the aniline Schiff base, thus reducing the reaction selectivity and yield. Paths of the above reactions all have some disadvantages, such as the use of toxic catalysts, long reaction time, high temperature, the formation of by-products and the low selectivity. Therefore, it is necessary to develop a green method for preparing the benzimidazole derivative by a chemoenzymatic method.

Quinoxaline and a derivative thereof are an important intermediates in organic synthesis, a compound containing a quinoxaline unit may be widely used in the field of medicines due to a unique structure, such as the manufacturing of cardiotonic agents, stimulants, antimalarial drugs, and powerful anti-tuberculosis and anti-bacterial agents, and the quinoxaline and the derivative thereof are also used in the fields of dye intermediates, polymer solar cells and luminescent materials, so that the research on the synthesis of the quinoxaline derivative has attracted the attention of scientific researchers. The commonly used methods for the quinoline derivative mainly include: the series cyclization of o-phenylenediamine and α-bromoketone; the synthesis by a three-component one-pot method with aromatic aldehyde, 6-aminoquinoxaline and tetronic acid as raw materials; the 1,3-dipolar cycloaddition of α-chloroquinoxaline-2-formaldehyde oxime and a sodium salt of ethyl acetoacetate; the oxidative condensation of α-bromoketone and aromatic 1,2-diamine; and the one-pot reaction of aromatic aldehyde and o-phenylenediamine. Commonly used catalysts comprise $Yb(OTf)_3$, $CuSO_4 5H_2O$, gallium triflate, zinc-L-proline, etc., and some of these methods have simple starting materials with low cost and high yield. However, there are some problems, such as a complex synthetic process, long reaction time, harsh reaction conditions, expensive or toxic catalysts, complicated post-treatment, and the defect of being not conducive to environmental protection.

The above synthetic methods for the nitrogen-containing heterocyclic compound and the derivative thereof generally have difficulties to be solved, such as the use of metal catalysts, acid-base conditions, high temperature, the formation of by-products and difficult post-treatment. Therefore, we have constructed a novel method for the efficient, economical and green synthesis of the nitrogen-containing heterocyclic compound and the derivative thereof by chemoenzymatic cascade catalysis.

SUMMARY

Object of the present invention: the technical problem to be solved by the present invention is to provide a method for preparing a nitrogen-containing heterocyclic compound and a derivative thereof by an chemoenzymatic cascade method in view of the deficiencies in the prior art.

Idea of the present invention: firstly, pure alcohol dehydrogenase is obtained through enzyme expression and purification, then the alcohol dehydrogenase is used as a catalyst and the alcohol is used as a substrate to construct an oxidation-reduction reaction; meanwhile, a regeneration system is formed by adding a catalytic amount of flavin molecule and coenzyme, the flavin molecule is used as a regeneration catalyst of the coenzyme, and oxidative coupling is performed on the alcohol dehydrogenase dependent on the coenzyme to form a regeneration cycle system of the coenzyme, and the biocatalytic alcohol is oxidized to generate aldehyde; and the generated aldehyde is further condensed with amine, and the nitrogen-containing heterocyclic compounds and derivatives thereof are obtained through further chemical oxidation. Specifically, the alcohol is generated into aldehyde and NADH under the action of the alcohol dehydrogenase and coenzyme $NAD^+$, and the flavin molecule regenerates coenzyme $NAD^+$ to generate aldehyde, and the generated aldehyde reacts with the amine to generate the nitrogen-containing heterocyclic compound and the derivative thereof under the chemical oxidation of the flavin molecule, thus forming a complete catalytic system.

In order to solve the above technical problems, the present invention discloses a method for preparing a nitrogen-containing heterocyclic compound and a derivative thereof by an enzymatic-chemical cascade method, comprising: in a solvent, taking an alcohol and an amine as raw materials, and reacting in a chemical chemoenzymatic cascade catalytic system consisting of an alcohol dehydrogenase, a flavin molecule and a coenzyme to obtain the nitrogen-containing heterocyclic compound and the derivative thereof.

A structural formula of the nitrogen-containing heterocyclic compound includes but is not limited to formula I:

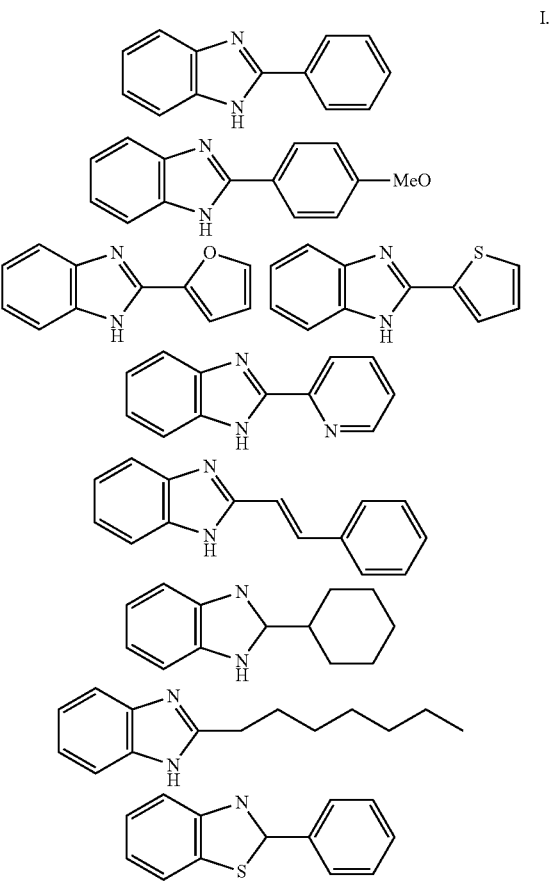

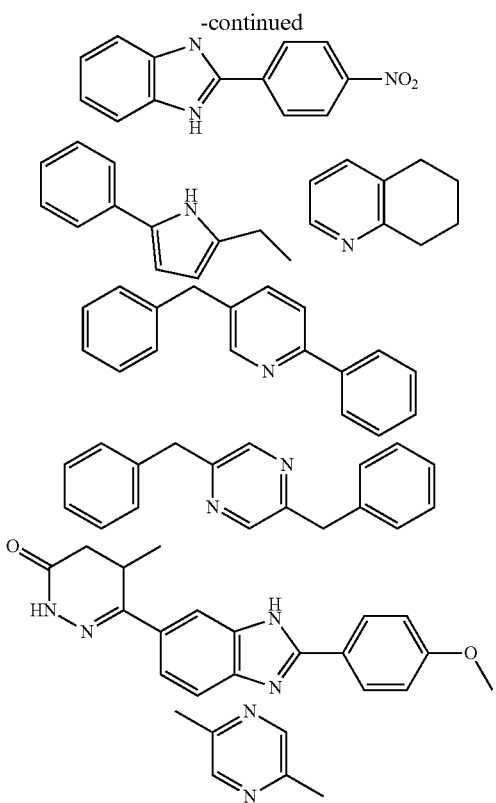

The alcohol is any one or a combination of fatty alcohol, naphthenic alcohol and aromatic alcohol; preferably, the alcohol is any one or a combination of benzyl alcohol, p-methoxybenzyl alcohol, 2-furanmethanol, 2-thiophene methanol, 2-pyridinemethanol, cinnamyl alcohol, n-octanol, cyclohexyl methanol, phenylethanol, cyclohexanol, phenylpropanol, phenylpropanolamine, 2-amino-1-propanol and p-methoxybenzyl alcohol; further preferably, the alcohol is any one or a combination of benzyl alcohol, p-methoxybenzyl alcohol, 2-furanmethanol, 2-pyridinemethanol, cinnamyl alcohol, n-octanol, cyclohexyl methanol, phenylethanol, phenylpropanolamine, 2-amino-1-propanol and p-methoxybenzyl alcohol; and more preferably, the alcohol is any one or a combination of benzyl alcohol, p-methoxybenzyl alcohol, 2-furanmethanol, cyclohexyl methanol, cinnamyl alcohol and phenylethanol.

A final concentration of the alcohol is 0.5 mM to 10 M; preferably, the final concentration of the alcohol is 1 mM to 10 mM; and further preferably, the final concentration of the alcohol is 5 mM.

The amine is any one or a combination of aromatic amine and fatty amine; preferably, the amine is naphthenic diamine; further preferably, the amine is any one or a combination of o-phenylenediamine, o-aminophenol, 3-aminopropanol, 3-amino-2-methylpropane-1-ol and 6-(3,4 diaminophenyl)-4,5 dihydro-5-methyl-3(2H)-phthalazinone; and more preferably, the amine is o-phenylenediamine.

A final concentration of the amine is 0.5 mM to 10 M; preferably, the final concentration of the amine is 1 mM to 10 mM; and further preferably, the final concentration of the amine is 6 mM.

When the alcohol contains —NH, that is, when the alcohol is alkylol amine, no additional amine is needed; preferably, a final concentration of the alkylol amine is 0.5 mM to 10 M; further preferably, the final concentration of the alkylol amine is 1 mM to 10 mM; and more preferably, the final concentration of the alkylol amine is 5 mM.

The alkylol amine is preferably 2-amino-1-propanol.

The alcohol dehydrogenase (enzymology number is EC 1.1.1.1) is any one or a combination of ethanol dehydrogenase (enzyme activity is 0.01 U/mL to 1,000 U/mL), horse liver alcohol dehydrogenase (enzyme activity is 0.01 U/mL to 1,000 U/mL), yeast alcohol dehydrogenase (enzyme activity is 0.01 U/mL to 1,000 U/mL) and mannitol dehydrogenase (enzyme activity is 0.01 U/mL to 1,000 U/mL); and preferably, the alcohol dehydrogenase is horse liver alcohol dehydrogenase.

Definition of enzyme activity: under specific conditions, an amount of enzyme required to convert one micromole of ethanol in one minute is one unit of activity (U). The temperature is set at 25° C., and other conditions are subjected to optimum conditions for the reaction.

A dosage of the alcohol dehydrogenase in the whole reaction system is 0.01 U/mL to 1,000 U/mL; preferably, the dosage of the alcohol dehydrogenase in the whole reaction system is 0.01 U/mL to 100 U/mL; further preferably, the dosage of the alcohol dehydrogenase in the whole reaction system is 0.01 U/mL to 10 U/mL; and more preferably, the dosage of the alcohol dehydrogenase in the whole reaction system is 0.01 U/mL to 100 U/mL.

The flavin molecule is any one of natural flavin and synthetic flavin analog; and preferably, the flavin molecule is synthetic flavin analog.

The natural flavin refers to FMN, FAD, and a structural formula of the natural flavin is shown as follows:

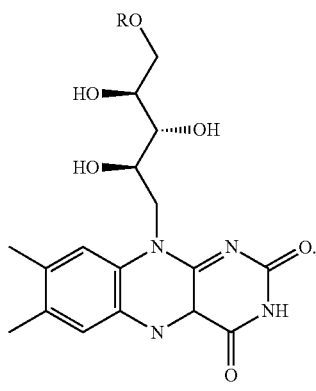

FMN: R = PO$_3^-$
FAD: R = ADP

The synthetic flavin analog is shown in formula II, which may be synthesized with reference to the prior art [1] or directly purchased;

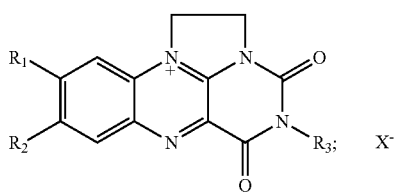

II wherein, $R_1$ and $R_2$ are each independently selected from hydrogen, methyl, trifluoromethyl, methoxy, halogen atom, nitro or amino; $R_3$ is selected from hydrogen, C1-C5 alkyl, phenyl or benzyl; and $X^-$ is selected from halide ion, nitrate or trifluoromethanesulfonate.

Preferably, the synthetic flavin analog is any one of 7-trifluoromethyl-N1,N10-vinyl isoalloxazine chloride, 8-chloro-1,10-ethylidene isoalloxazine chloride shown in formula II-2 and 1,10-ethylidene isoalloxazine chloride shown in formula II-3.

1.

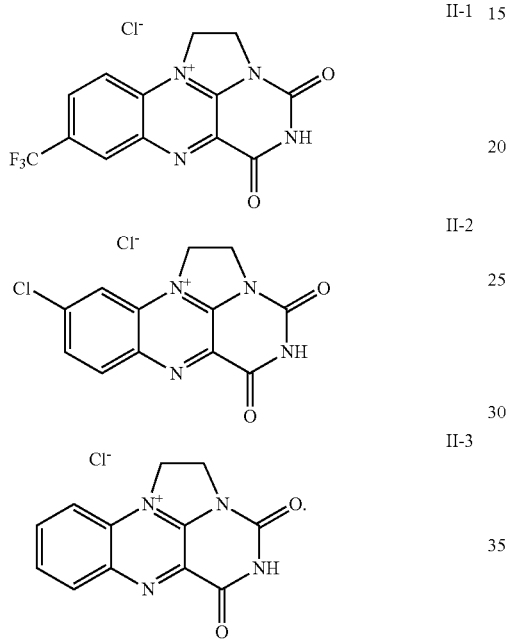

A final concentration of the flavin molecule is 0.1 mM to 1 M; preferably, the final concentration of the flavin molecule is 0.5 mM to 1 M; and further preferably, the final concentration of the flavin molecule is 0.5 mM.

The coenzyme is any one or a combination of natural coenzyme and fatty amine; and preferably, the coenzyme is natural coenzyme.

The coenzyme is any one or a combination of $NADP^+$ and $NAD^+$; and preferably, the coenzyme is $NAD^+$.

A final concentration of the coenzyme is 0.1 mM to 1 M.

The solvent is a buffer solution; preferably, the solvent is an aqueous buffer solution; further preferably, the solvent is any one of potassium phosphate buffer, sodium phosphate buffer and Tris-HCl buffer; more preferably, the solvent is potassium phosphate buffer; more further preferably, the solvent is potassium phosphate buffer with a pH of 4 to 10; and most preferably, the solvent is 50 mM potassium phosphate aqueous buffer solution with a pH of 7.

The reaction is performed at a pH of 4 to 10 and at 30° C. to 70° C. for 2 hours to 60 hours.

The above reaction is carried out in an air atmosphere.

Beneficial effects: compared with the prior art, the present invention has the following advantages.

(1). The present invention is a green and economical chemoenzymatic cascade method, and is used for synthesizing nitrogen-containing heterocyclic compounds and derivatives thereof.

(2) Compared with a common toxic chemical catalyst, the alcohol dehydrogenase is selected as a catalyst in the present invention, which has the characteristics of high substrate specificity, no pollution, high catalytic efficiency, no toxic solvents and simple post-treatment. The solvent is an aqueous buffer solution, no toxic solvent is used, no by-products are generated, and the obtained products are easy to separate.

(3). The flavin molecule in the present invention has two functions, one is to form a former enzymatic regeneration system, and the other is to be used as an oxidizing agent in a later chemical method, such that no other oxidizing agents need to be added throughout the whole cascade reaction.

BRIEF DESCRIPTION OF THE DRAWINGS

The advantages of the above and/or other aspects of the present invention will become more apparent by further explaining the present invention with reference to the following drawings and detailed description.

DETAILED DESCRIPTION

The experimental methods used in the following embodiments are all conventional methods unless otherwise specified. The reagents and materials used are commercially available unless otherwise specified.

The present invention will be further described in detail below with reference to the specific embodiments. It should be understood that the following embodiments are only used to illustrate the present invention and are not used to limit the scope of the present invention. In the following embodiments, concentrations of alcohol, amine, flavin molecule and coenzyme all refer to final concentrations in the system; and a dosage of the alcohol dehydrogenase is relative to the whole reaction system.

A method for producing nitrogen-containing heterocyclic compounds and derivatives thereof of the present invention uses an alcohol as a substrate, uses an $NAD^+$-dependent horse liver alcohol dehydrogenase to catalyze the production of aldehyde with a catalytic amount of synthetic flavin analog and coenzyme in an oxygen or air atmosphere, and the generated aldehyde reacts with the amine to generate the nitrogen-containing heterocyclic compound and the derivative thereof under the chemical oxidation of the synthetic flavin analog.

In the following embodiments, the enzyme activity of the horse liver alcohol dehydrogenase is 5 U/mL.

Embodiment 1

Figure 1:
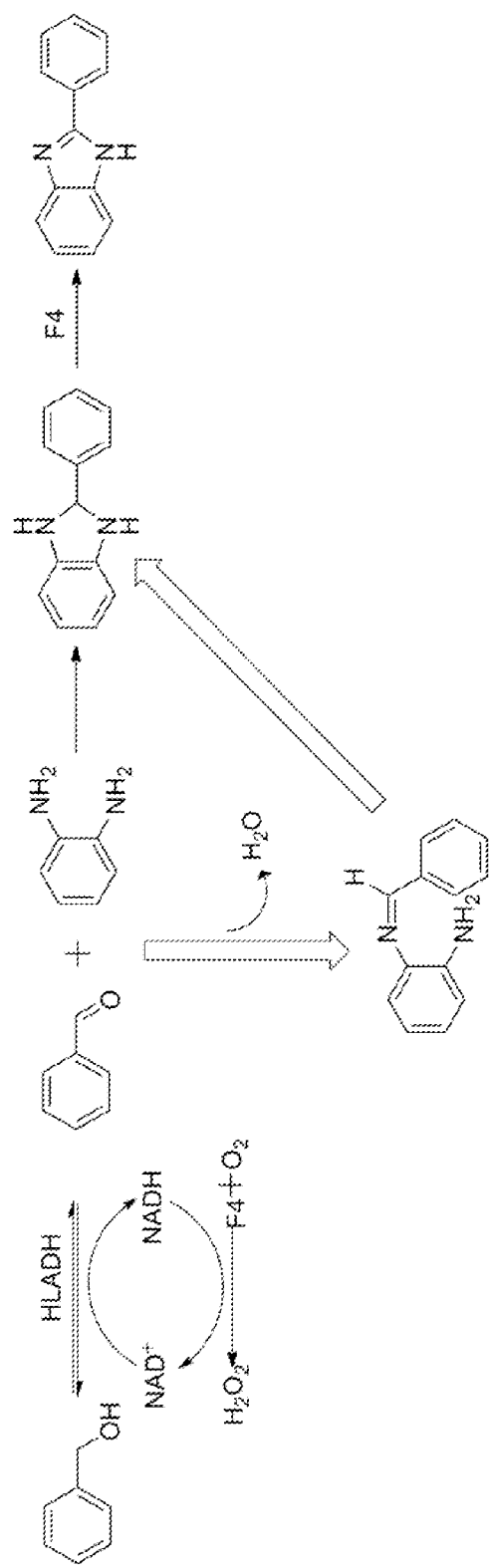
FIG. 1 is a reaction schematic diagram of Embodiment 1, wherein HLADH is a horse liver alcohol dehydrogenase and F4 is a synthetic flavin analog.

Benzaldehyde was prepared by coupling 7-trifluoromethyl-N1,N10-vinyl isoalloxazine chloride as a catalyst for regenerating $NAD^+$ with a horse liver alcohol dehydrogenase to catalyze benzyl alcohol. By using the 7-trifluoromethyl-N1,N10-vinyl isoalloxazine chloride as an oxidizing agent, the generated benzaldehyde reacted with 1,2-phenylenediamine to generate 2-phenylbenzimidazole, and the reaction schematic diagram was shown in FIG. 1. Benzyl alcohol was generated into benzaldehyde in a regeneration reaction system composed of synthetic flavin analog and coenzyme by using the horse liver alcohol dehydrogenase as a catalyst. The generated benzaldehyde continued to react with 1,2-phenylenediamine, and a final product 2-phenylbenzimidazole was generated under the oxidation catalysis of the synthetic flavin analog.

Figure 2:
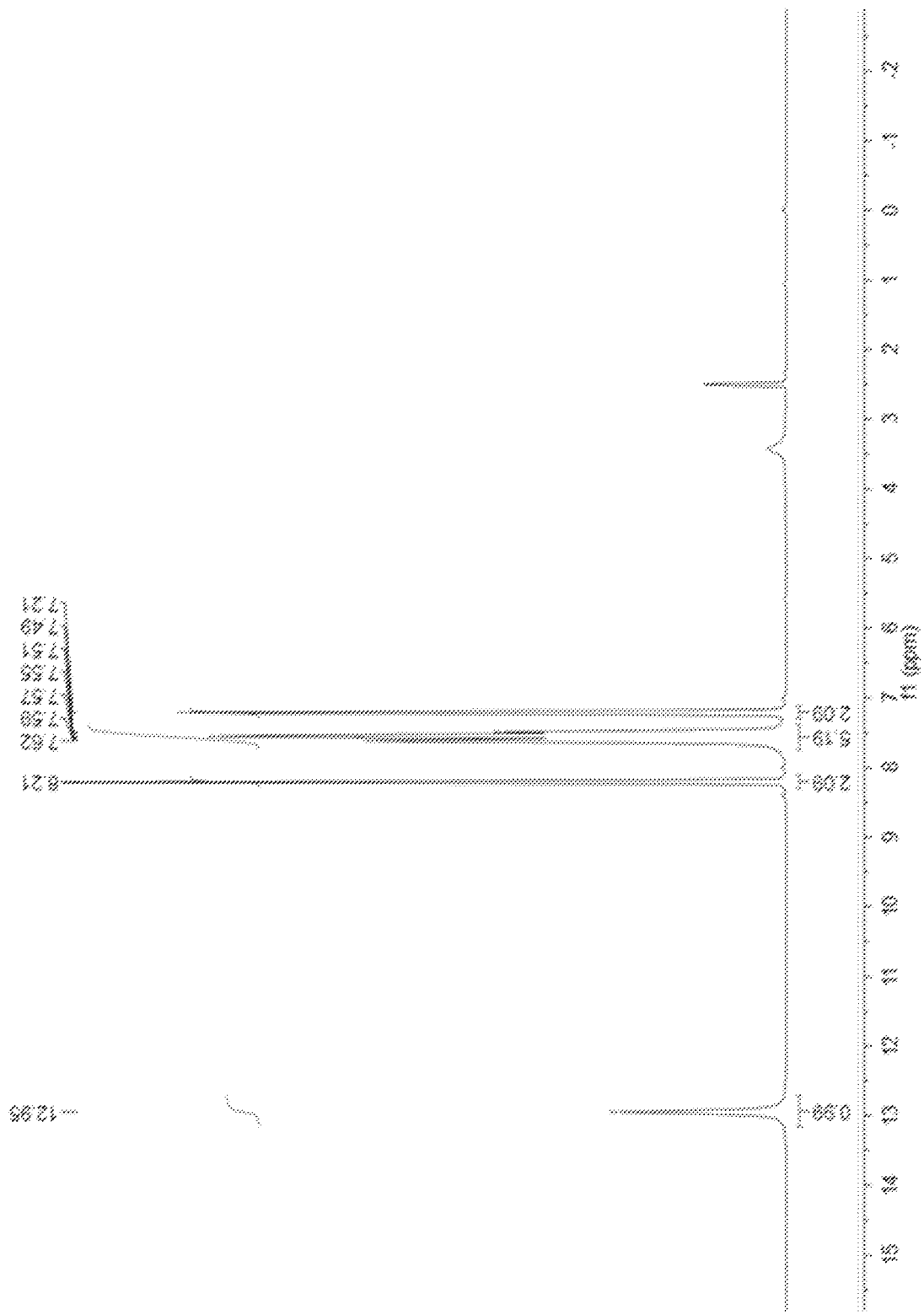
FIG. 2 is a hydrogen spectrum of a product 2-phenylbenzimidazole in Embodiment 1.
Figure 3:
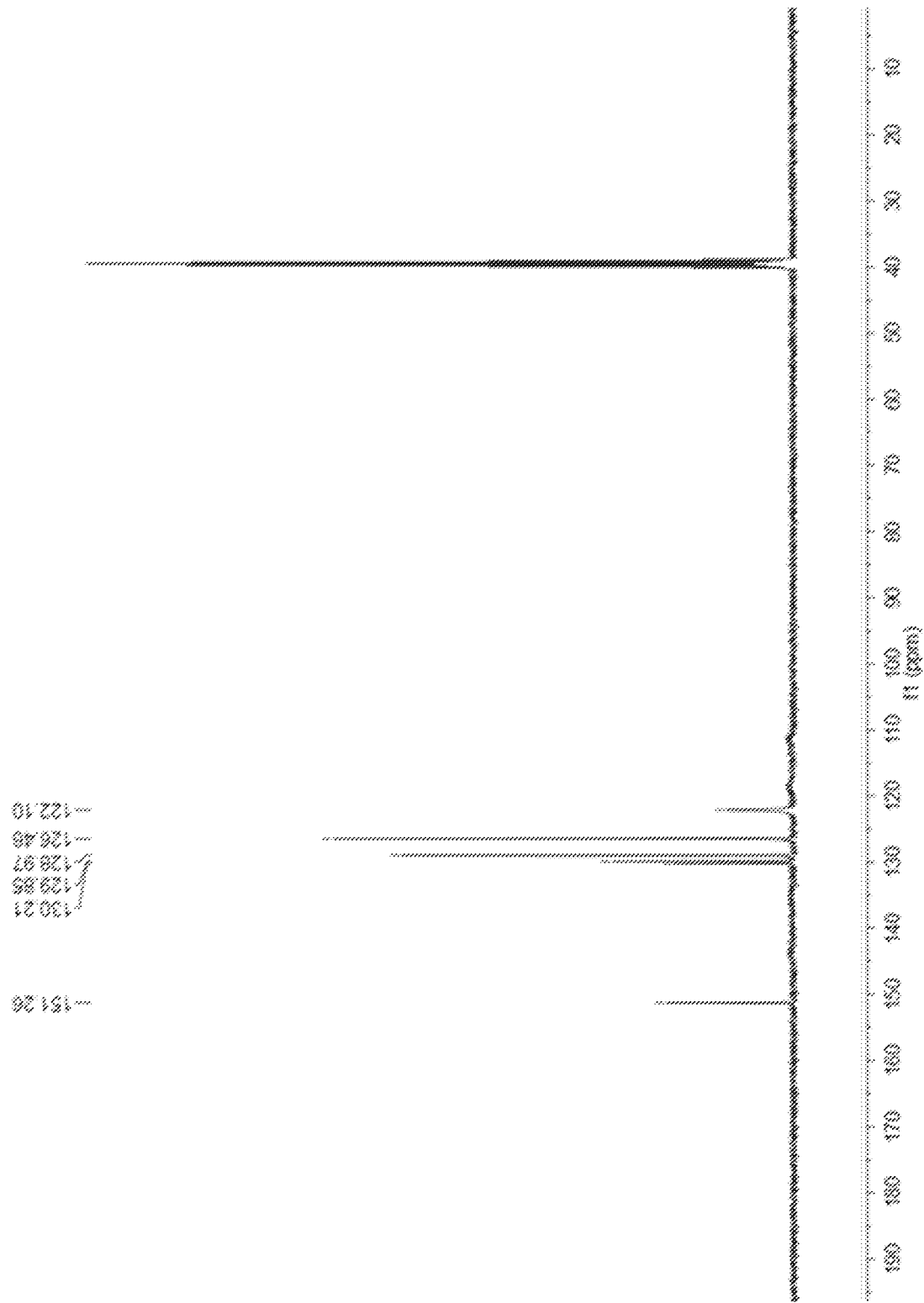
FIG. 3 is a carbon spectrum of the product 2-phenylbenzimidazole in Embodiment 1.

In a shaker at 30° C. and 200 rpm, in 2 mL of 100 mM potassium phosphate buffer with a pH of 7, 5 mM of benzyl alcohol, 1 mM of $NAD^+$, 0.5 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 48 hours. The yield was 99% through quantitative analysis by HPLC. A NMR of the product was shown in FIG. 2 and FIG. 3.

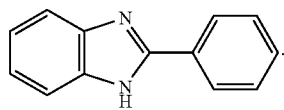

Comparative Example 1

As in Embodiment 1, the other amounts of the test were kept constant, but the amount of 7-trifluoromethyl-N1,N10-vinyl isoalloxazine chloride was changed to 0.1 mM, and the reaction lasted for 48 hours. The yield was 68% through quantitative analysis by HPLC.

Comparative Example 2

As in Embodiment 1, the other amounts of the control test were kept constant, but the amount of 7-trifluoromethyl-N1,N10-vinyl isoalloxazine chloride was changed to 0.2 mM. The reaction lasted for 48 hours. The yield was 76% through quantitative analysis by HPLC.

Embodiment 2

4-methoxybenzaldehyde was prepared by coupling 7-trifluoromethyl-N1,N10-vinyl isoalloxazine chloride as a catalyst for regenerating $NAD^+$ with a horse liver alcohol dehydrogenase to catalyze 4-methoxybenzyl alcohol. By using the 7-trifluoromethyl-N1,N10-vinyl isoalloxazine chloride as an oxidizing agent, the generated p-methoxybenzaldehyde reacted with 1,2-phenylenediamine to generate 2-(4-methoxyphenyl)benzimidazole.

Figure 4:
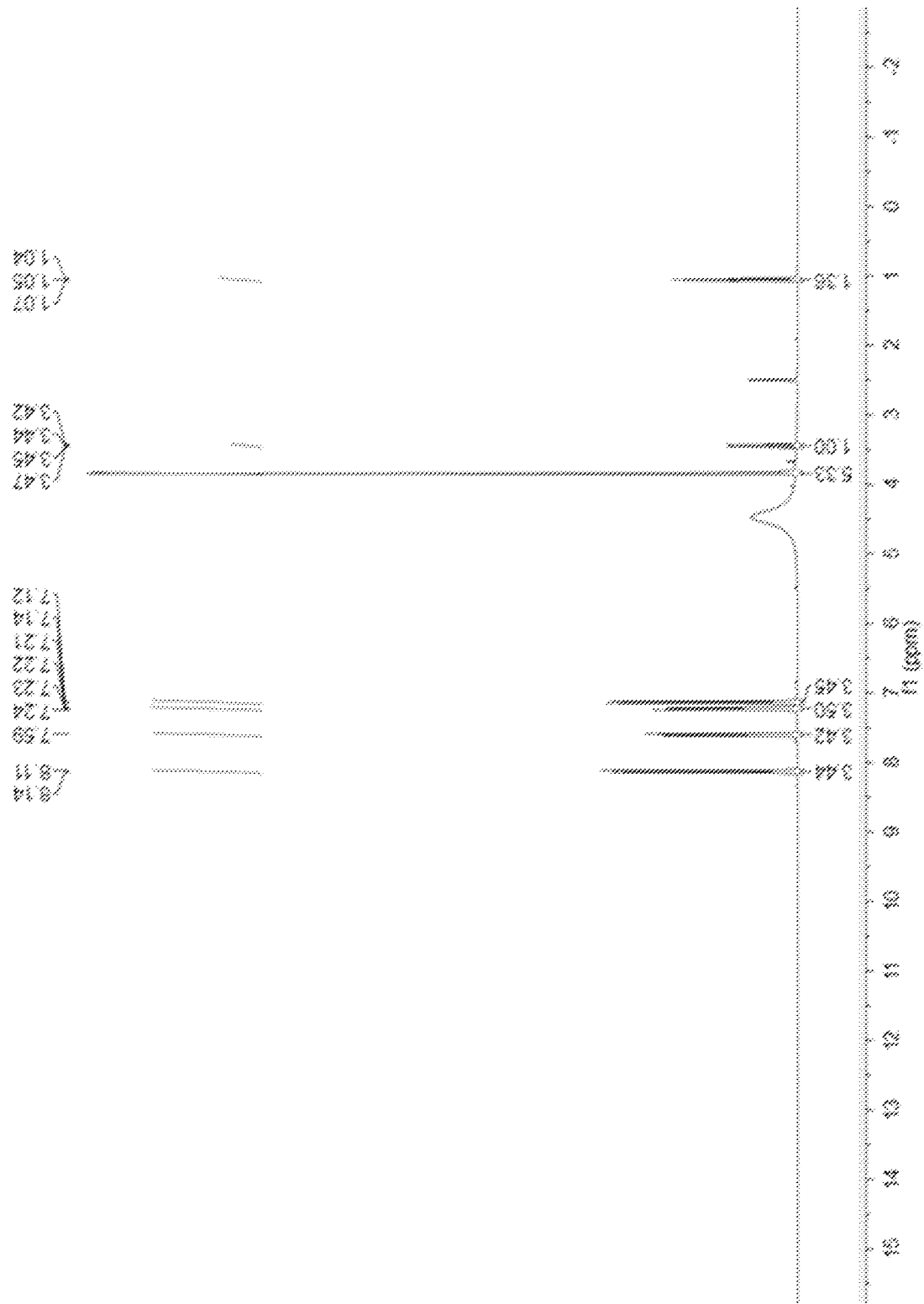
FIG. 4 is a hydrogen spectrum of a product 2-(4-methoxyphenyl)benzimidazole in Embodiment 2.
Figure 5:
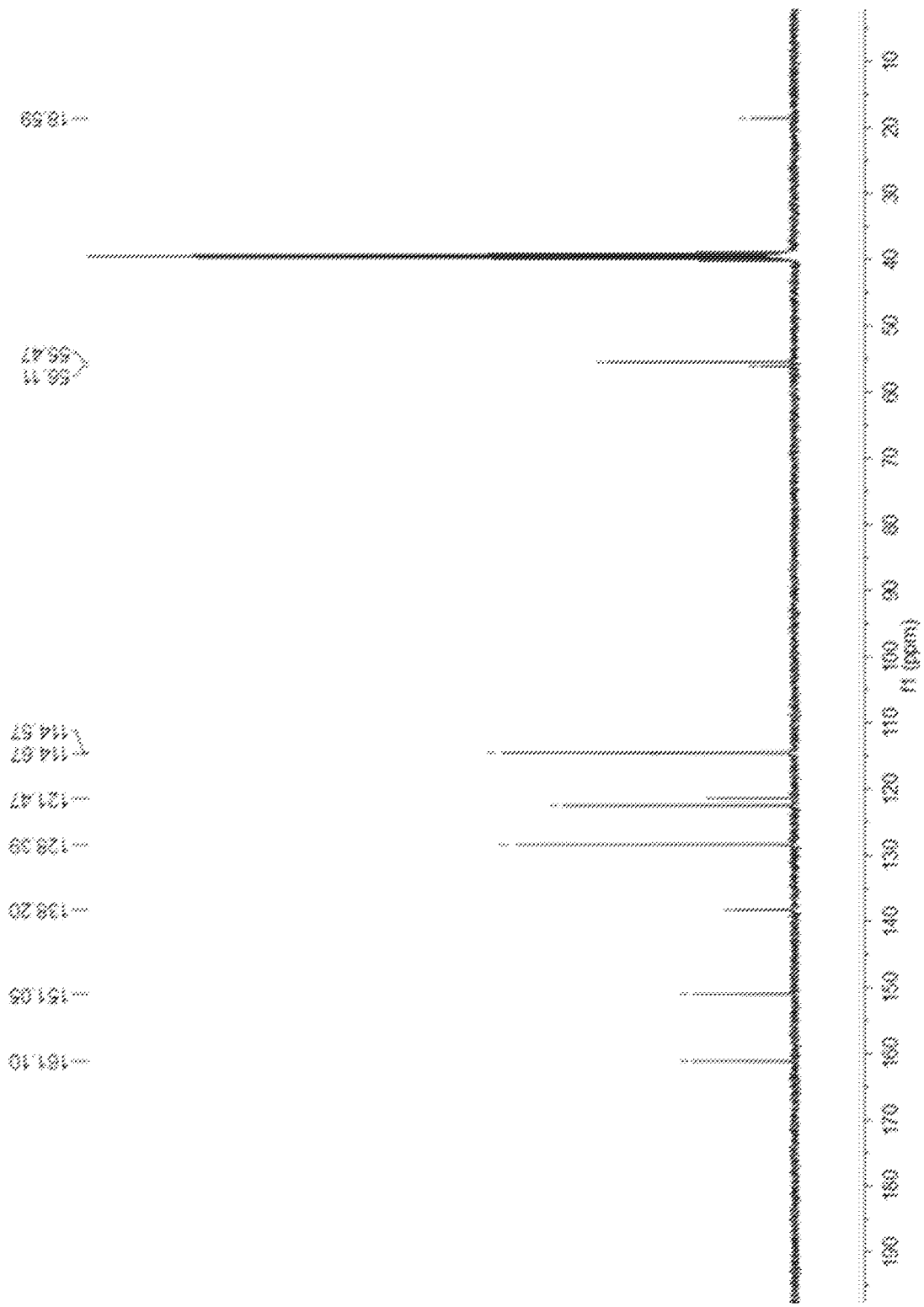
FIG. 5 is a carbon spectrum of the product 2-(4-methoxyphenyl)benzimidazole in Embodiment 2.

In a shaker at 30° C. and 200 rpm, in 2 mL of 100 mM potassium phosphate buffer with a pH of 7, 5 mM of p-methoxybenzyl alcohol, 1 mM of $NAD^+$, 0.5 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 4 hours. The yield was 99% through quantitative analysis by HPLC. A NMR of the product was shown in FIG. 4 and FIG. 5.

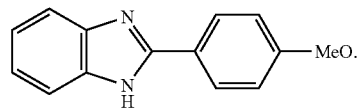

Embodiment 3

2-furaldehyde was prepared by coupling 7-trifluoromethyl-N1,N10-vinyl isoalloxazine chloride as a catalyst for regenerating $NAD^+$ with a horse liver alcohol dehydrogenase to catalyze 2-furanmethanol. By using the 7-trifluoromethyl-N1,N10-vinyl isoalloxazine chloride as an oxidizing agent, the generated 2-furaldehyde reacted with 1,2-phenylenediamine to generate fuberidazole.

Figure 6:
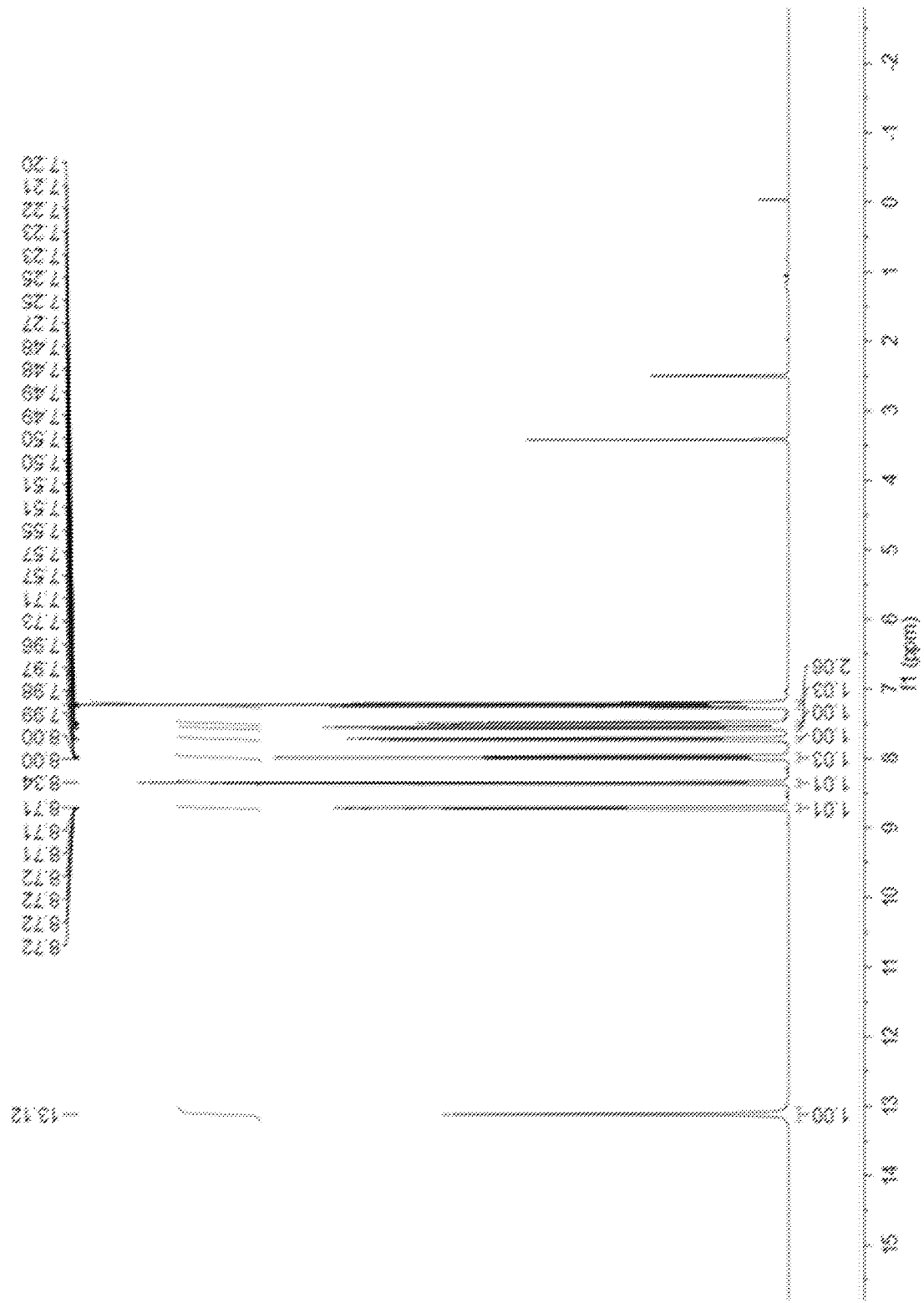
FIG. 6 is a hydrogen spectrum of a product 2-furolbenzimidazole in Embodiment 3.
Figure 7:
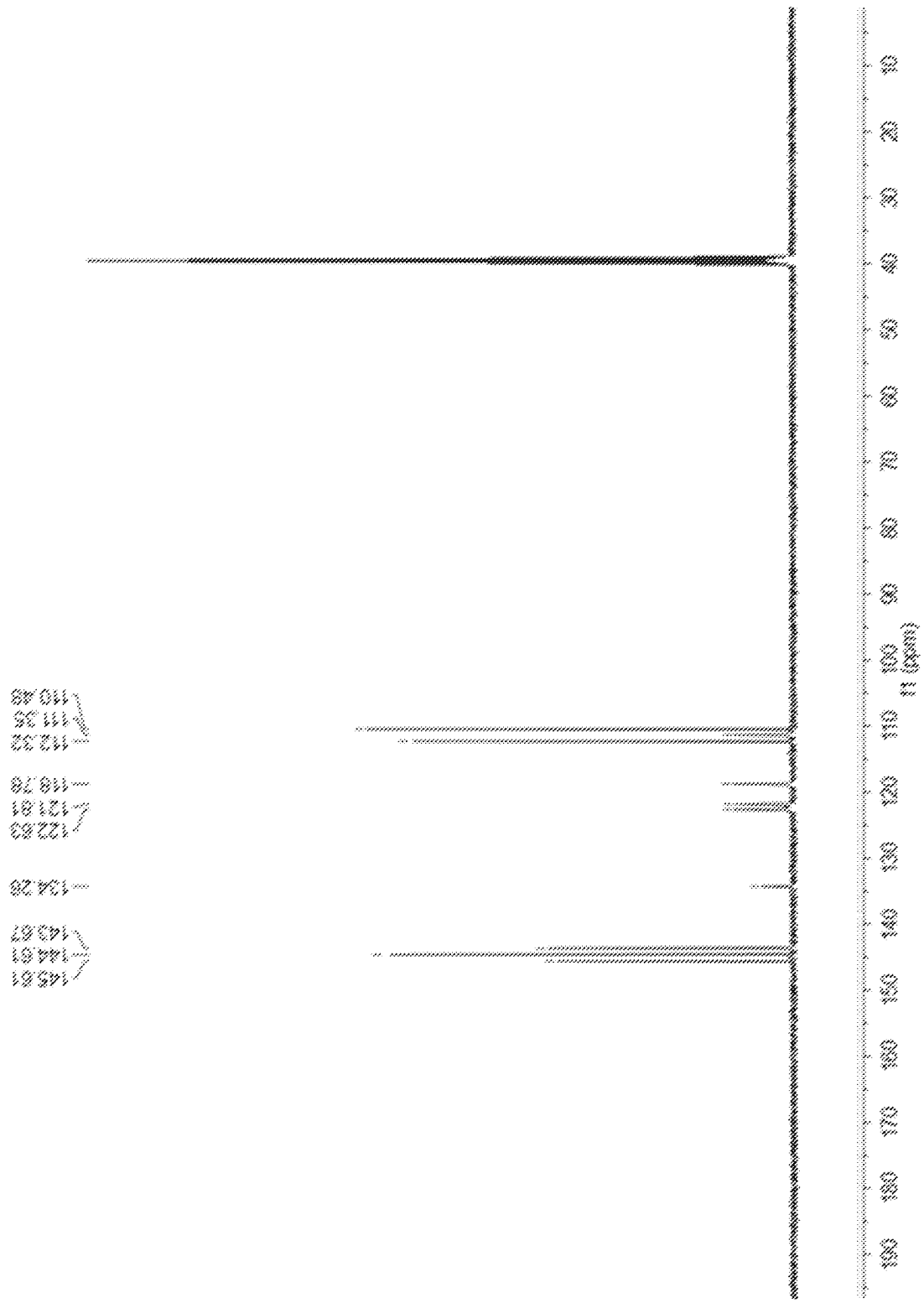
FIG. 7 is a carbon spectrum of the product 2-furolbenzimidazole in Embodiment 3.

In a shaker at 30° C. and 200 rpm, in 2 mL of 100 mM potassium phosphate buffer with a pH of 7, 5 mM of 2-furanmethanol, 1 mM of $NAD^+$, 1 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 12 hours. The yield was 88% through quantitative analysis by HPLC. A NMR of the product was shown in FIG. 6 and FIG. 7.

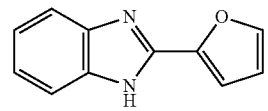

Comparative Example 3

As in Embodiment 3, the other amounts of the test were kept constant, but the amount of 7-trifluoromethyl-N1,N10-vinyl isoalloxazine chloride was changed to 0.5 mM, and the reaction lasted for 24 hours. The yield was 67% through quantitative analysis by HPLC.

Embodiment 4

2-thiophene methanol was prepared by coupling 7-trifluoromethyl-N1,N10-vinyl isoalloxazine chloride as a catalyst for regenerating NAD⁺ with a horse liver alcohol dehydrogenase to catalyze 2-thiophene methanol. By using the 7-trifluoromethyl-N1,N10-vinyl isoalloxazine chloride as an oxidizing agent, the generated 2-thiophene formaldehyde reacted with 1,2-phenylenediamine to generate 2-(2-thienyl)-1H-benzimidazole.

Figure 8:
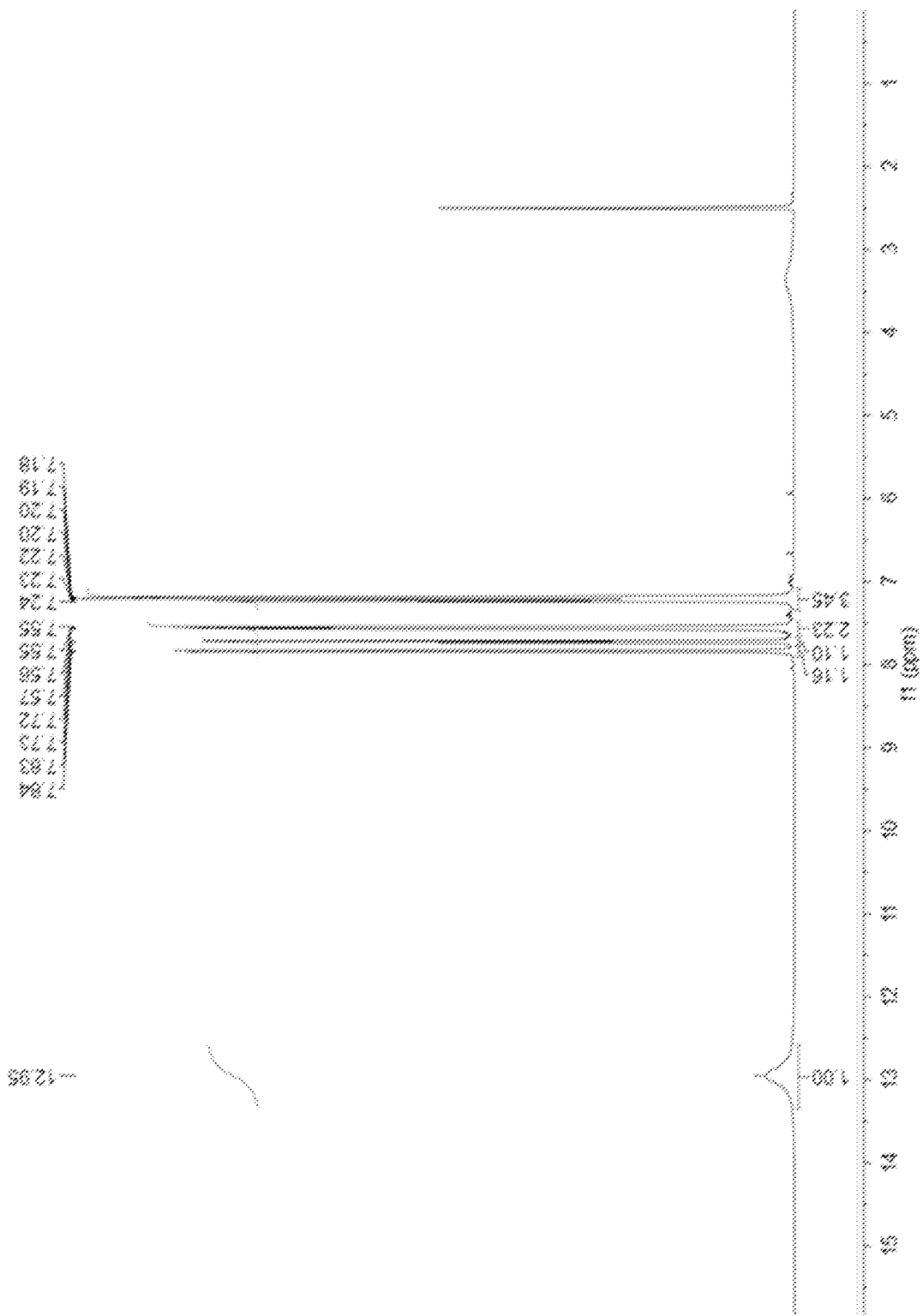
FIG. 8 is a hydrogen spectrum of a product 2-thienylbenzimidazole in Embodiment 4.
Figure 9:
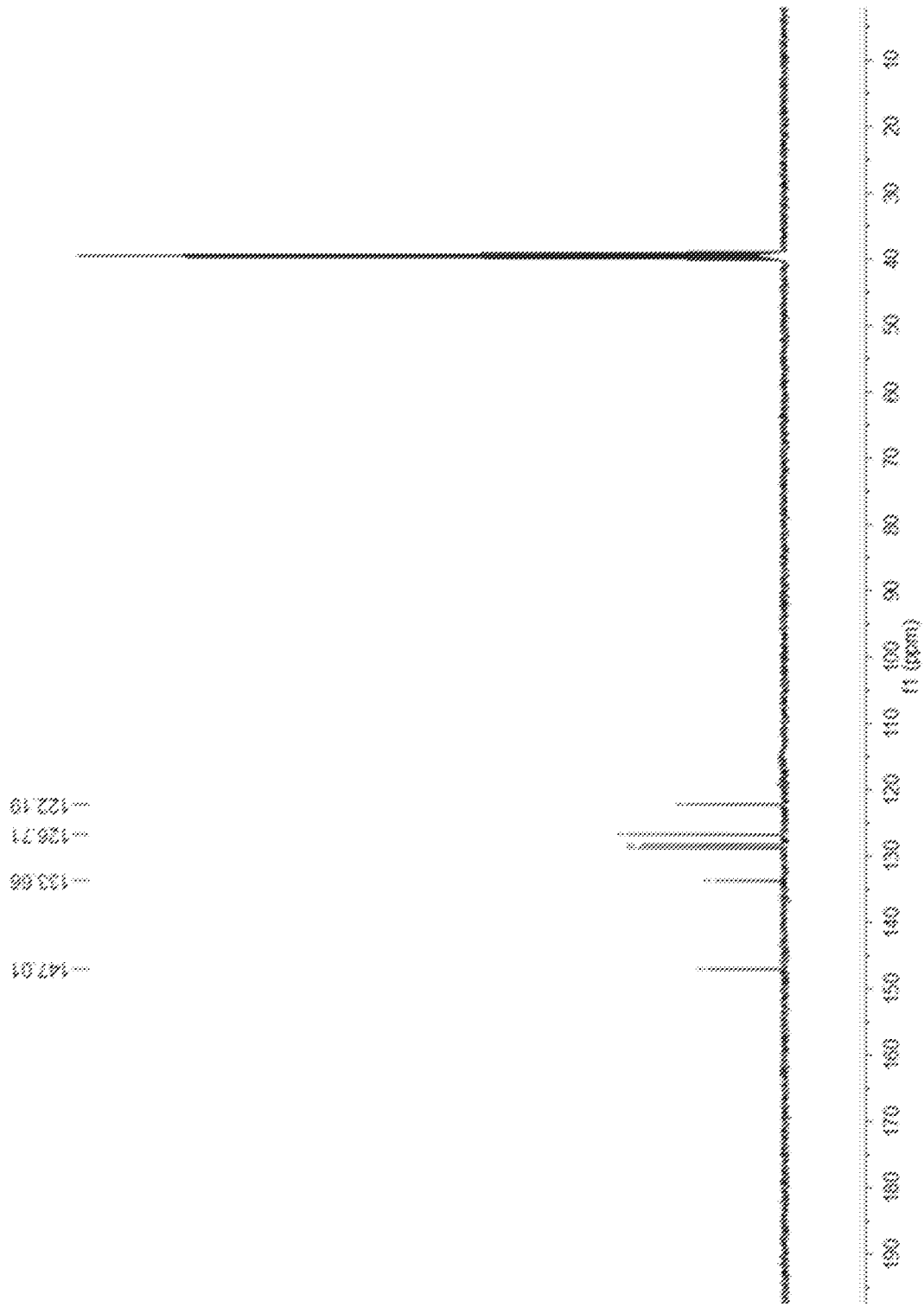
FIG. 9 is a carbon spectrum of the product 2-thienylbenzimidazole in Embodiment 4.

In a shaker at 30° C. and 200 rpm, in 2 mL of 100 mM potassium phosphate buffer with a pH of 7, 5 mM of 2-thiophene methanol, 1 mM of NAD+, 1 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 24 hours. The yield was 57% through quantitative analysis by HPLC. A NMR of the product was shown in FIG. 8 and FIG. 9.

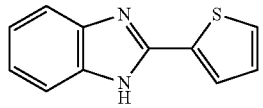 [SMILES: c1csc(-c2nc3ccccc3[nH]2)c1]

Embodiment 5

2-pyridinecarboxaldehyde was prepared by coupling 7-trifluoromethyl-N1,N10-vinyl isoalloxazine chloride as a catalyst for regenerating NAD⁺ with a horse liver alcohol dehydrogenase to catalyze 2-pyridinemethanol. By using the 7-trifluoromethyl-N1,N10-vinyl isoalloxazine chloride as an oxidizing agent, the generated 2-pyridinecarboxaldehyde reacted with 1,2-phenylenediamine to generate 2-(2-pyridyl)-1H-benzimidazole.

Figure 10:
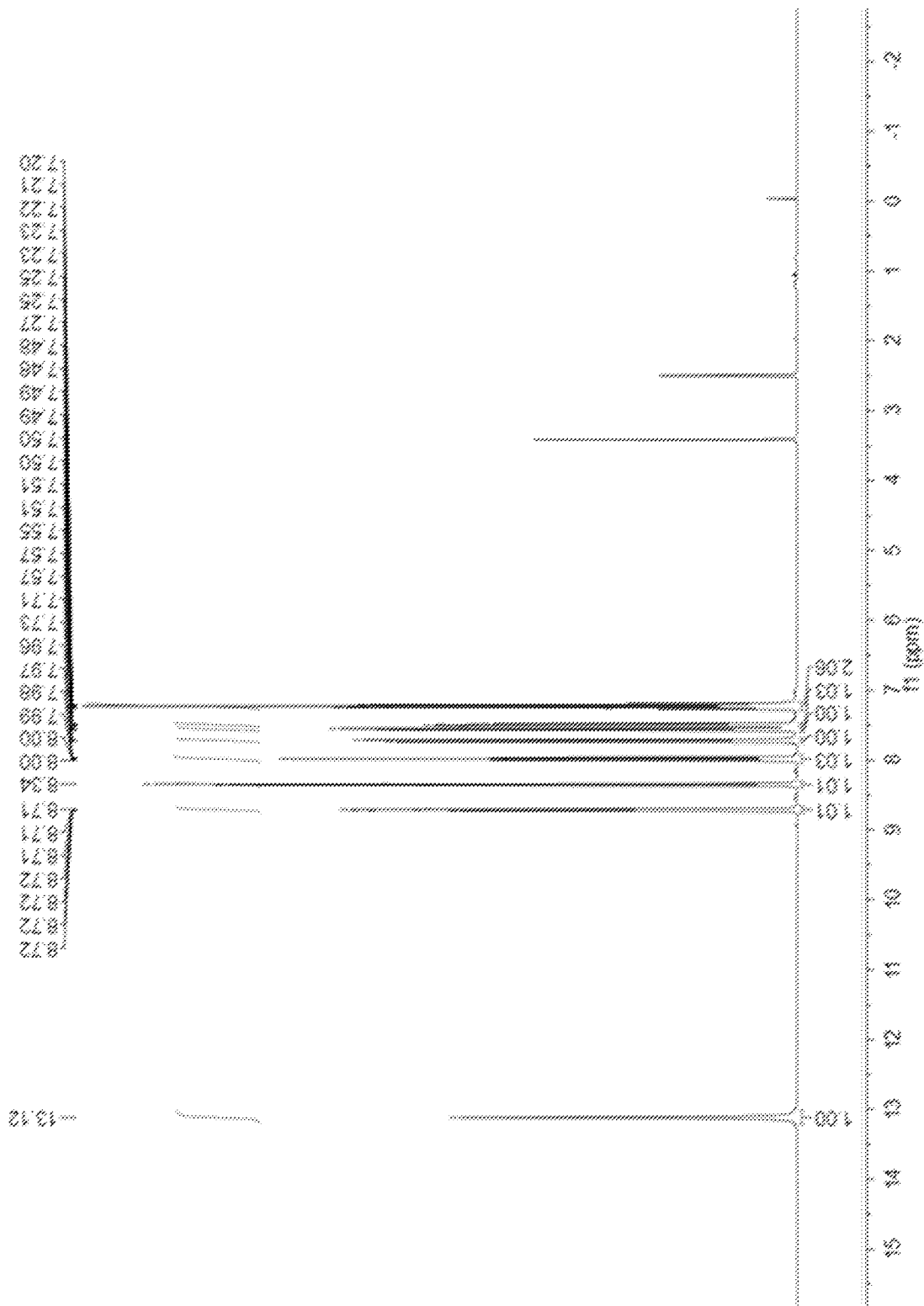
FIG. 10 is a hydrogen spectrum of a product 2-pyridylbenzimidazole in Embodiment 5.
Figure 11:
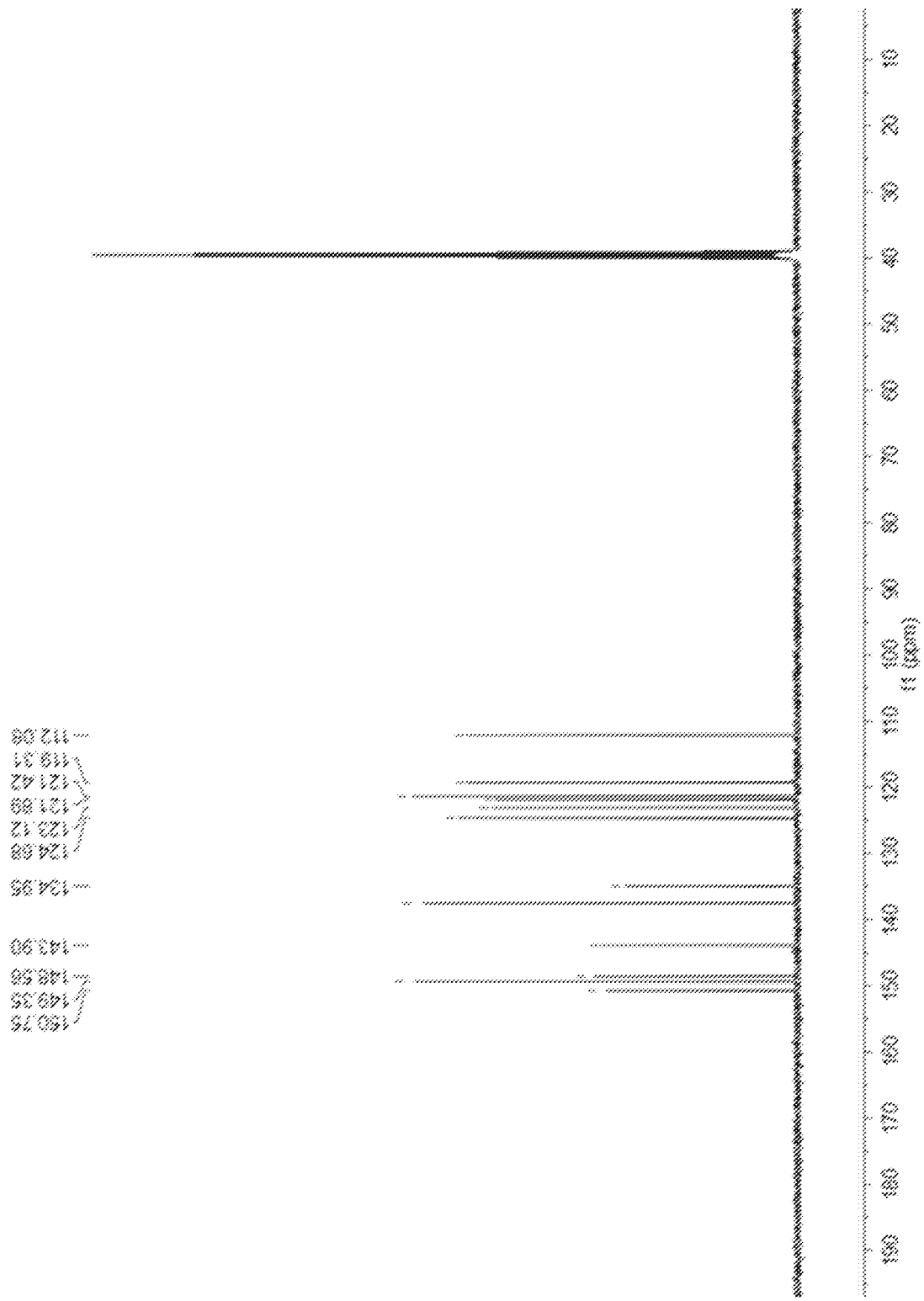
FIG. 11 is a carbon spectrum of the product 2-pyridylbenzimidazole in Embodiment 5.

In a shaker at 30° C. and 200 rpm, in 2 mL of 100 mM potassium phosphate buffer with a pH of 7, 5 mM of 2-pyridinemethanol, 1 mM of NAD+, 1 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 24 hours. The yield was 87% through quantitative analysis by HPLC. A NMR of the product was shown in FIG. 10 and FIG. 11.

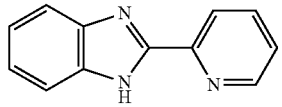 [SMILES: c1ccc(-c2nc3ccccc3[nH]2)nc1]

Comparative Example 4

As in Embodiment 5, the other amounts of the test were kept constant, but the amount of 7-trifluoromethyl-N1,N10-vinyl isoalloxazine chloride was changed to 2 mM, and the reaction lasted for 24 hours. The yield was 63% through quantitative analysis by HPLC.

Embodiment 6

Cinnamaldehyde was prepared by coupling 7-trifluoromethyl-N1,N10-vinyl isoalloxazine chloride as a catalyst for regenerating NAD⁺ with a horse liver alcohol dehydrogenase to catalyze cinnamyl alcohol. By using the 7-trifluoromethyl-N1,N10-vinyl isoalloxazine chloride as an oxidizing agent, the generated cinnamaldehyde reacted with 1,2-phenylenediamine to generate 2-(2-phenylvinyl)-1H-benzimidazole.

In a shaker at 30° C. and 200 rpm, in 2 mL of 100 mM potassium phosphate buffer with a pH of 7, 5 mM of cinnamyl alcohol, 1 mM of NAD⁺, 0.5 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 12 hours. The yield was 82% through quantitative analysis by HPLC.

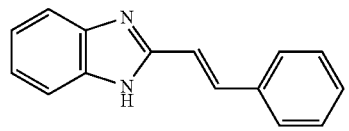 [SMILES: C(=C\c1nc2ccccc2[nH]1)/c1ccccc1]

Embodiment 7

Octanal was prepared by coupling 7-trifluoromethyl-N1,N10-vinyl isoalloxazine chloride as a catalyst for regenerating NAD⁺ with a horse liver alcohol dehydrogenase to catalyze n-octanol. By using the 7-trifluoromethyl-N1,N10-vinyl isoalloxazine chloride as an oxidizing agent, the generated octanal reacted with 1,2-phenylenediamine to generate 2-(2-heptyl)-benzimidazole.

Figure 12:
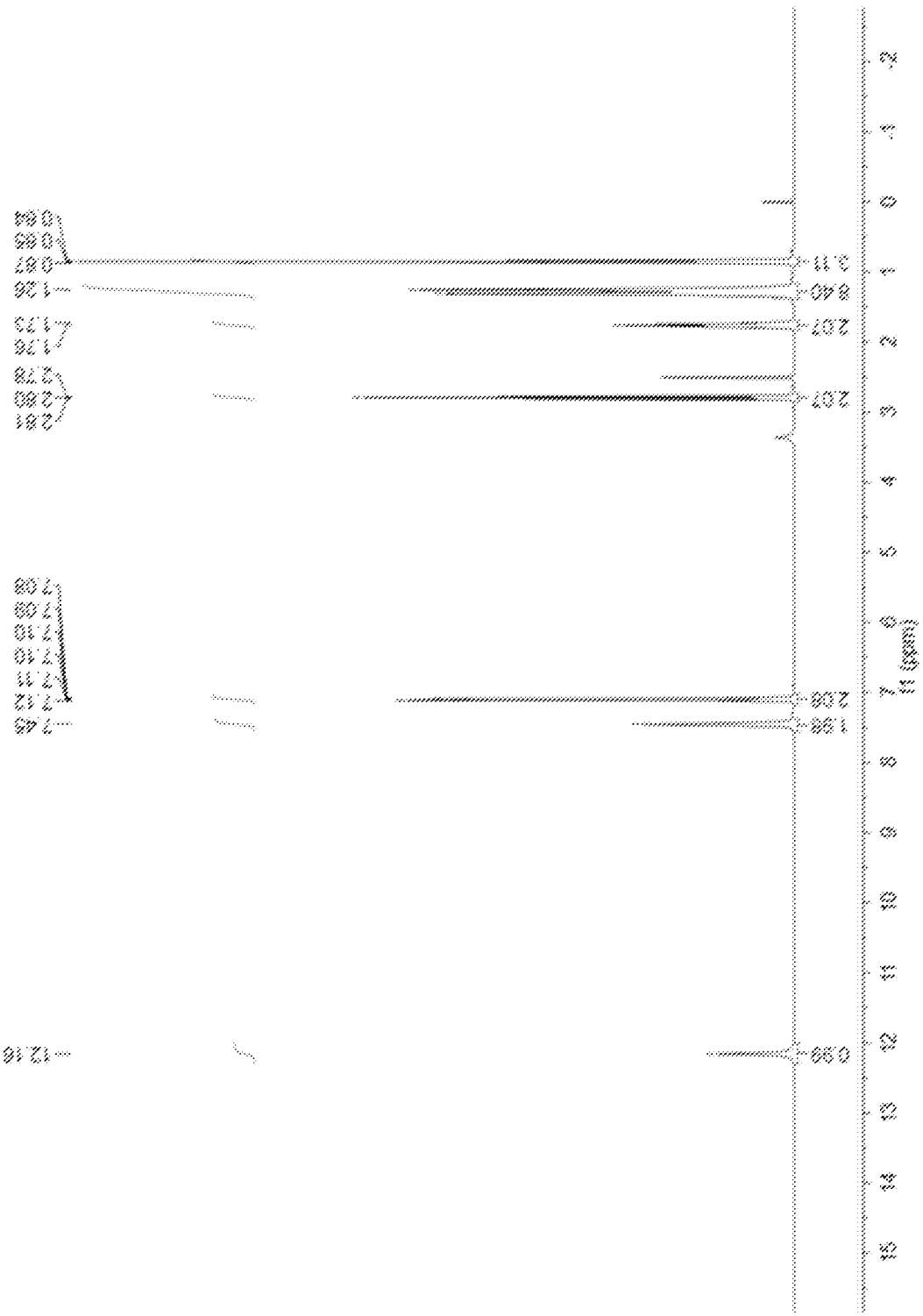
FIG. 12 is a hydrogen spectrum of a product 2-heptylbenzimidazole in Embodiment 7.
Figure 13:
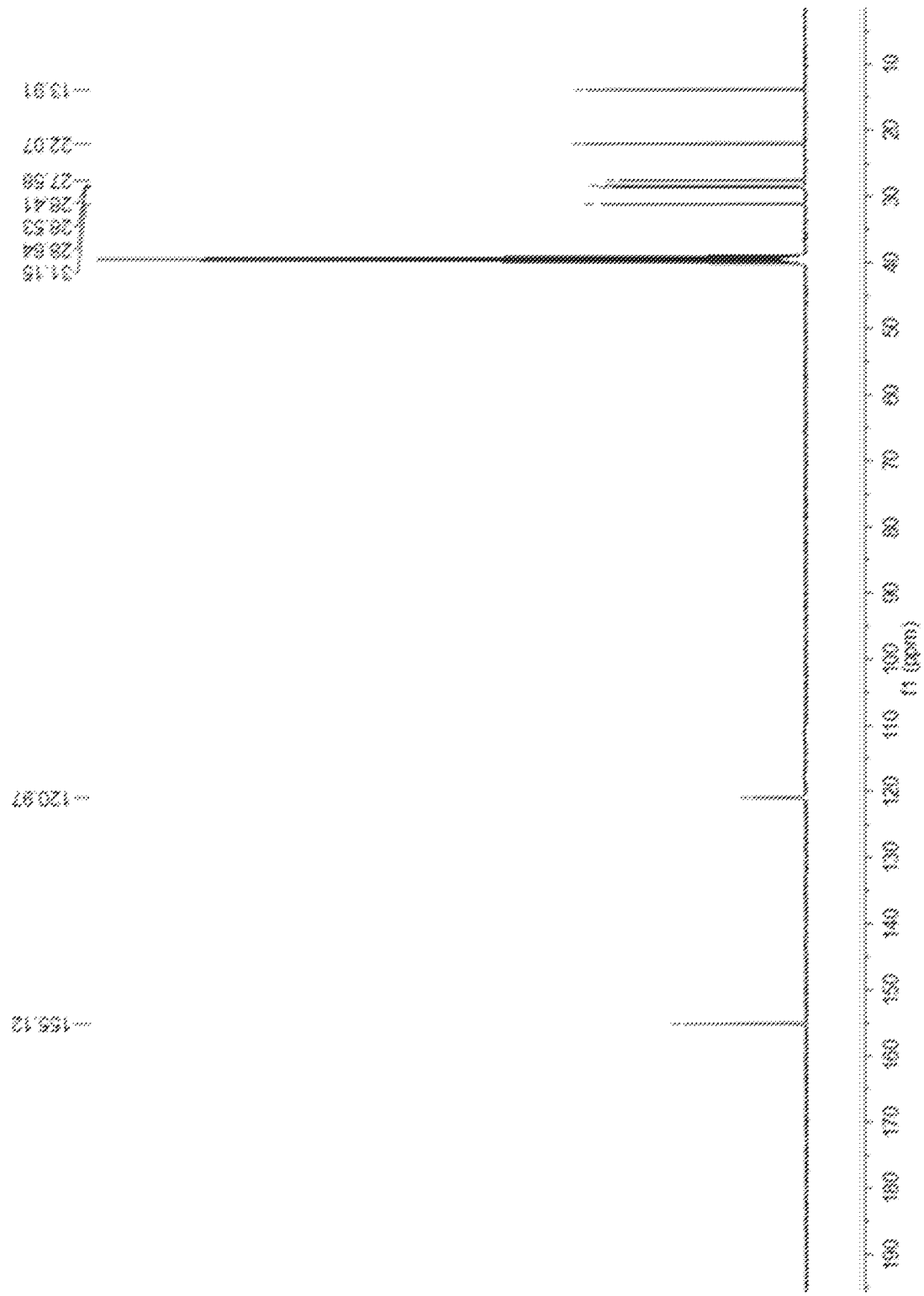
FIG. 13 is a carbon spectrum of the product 2-heptylbenzimidazole in Embodiment 7.

In a shaker at 30° C. and 200 rpm, in 2 mL of 100 mM potassium phosphate buffer with a pH of 7, 5 mM of n-octanol, 1 mM of NAD⁺, 1 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 12 hours. The yield was 72 through quantitative analysis by HPLC. A NMR of the product was shown in FIG. 12 and FIG. 13

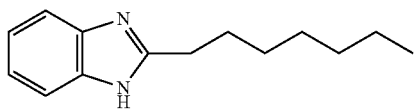 [SMILES: CCCCCCCc1nc2ccccc2[nH]1]

Embodiment 8

Cyclohexyl formaldehyde was prepared by coupling 7-trifluoromethyl-N1,N10-vinyl isoalloxazine chloride as a catalyst for regenerating NAD⁺ with a horse liver alcohol dehydrogenase to catalyze cyclohexyl methanol. By using the 7-trifluoromethyl-N1,N10-vinyl isoalloxazine chloride as an oxidizing agent, the generated cyclohexyl formaldehyde reacted with 1,2-phenylenediamine to generate 2-(cyclohexyl)-1H-benzimidazole.

Figure 14:
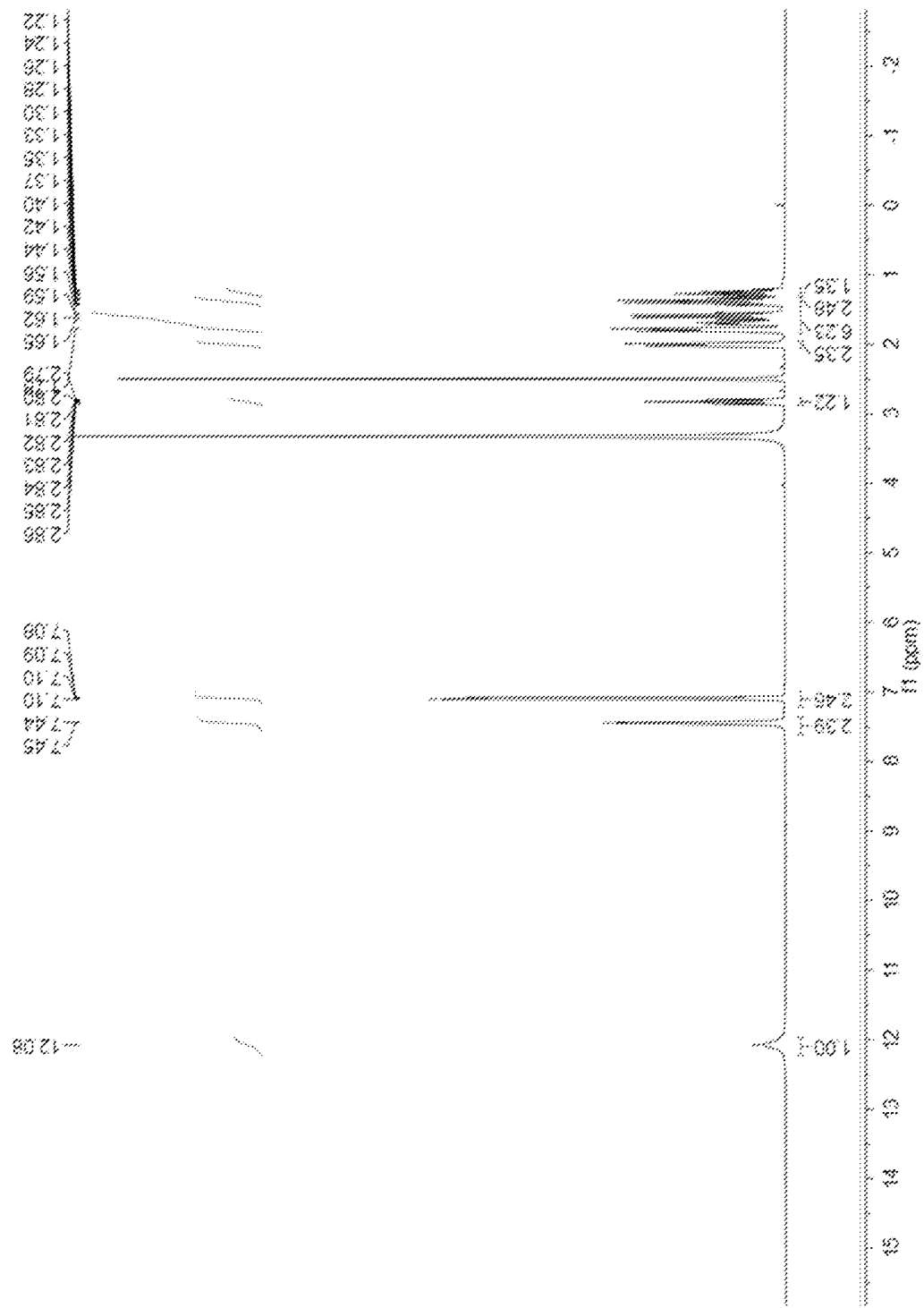
FIG. 14 is a hydrogen spectrum of a product 2-cyclohexyl-benzimidazole in Embodiment 8.
Figure 15:
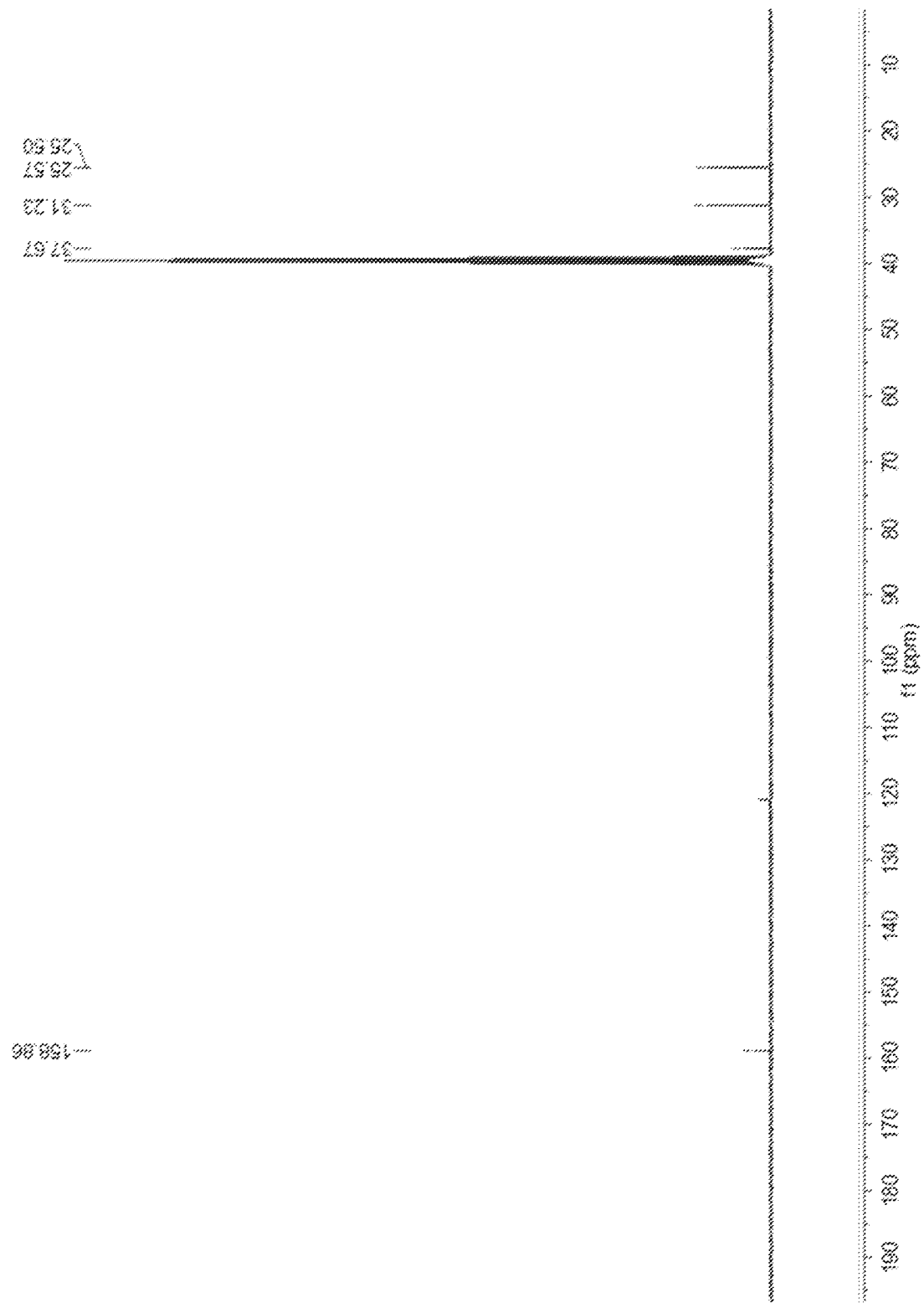
FIG. 15 is a carbon spectrum of the product 2-cyclohexylbenzimidazole in Embodiment 8.

In a shaker at 30° C. and 200 rpm, in 2 mL of 100 mM potassium phosphate buffer with a pH of 7, 5 mM of cyclohexyl methanol, 1 mM of NAD⁺, 0.5 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 48 hours. The yield was 91% through quantitative analysis by HPLC. A NMR of the product was shown in FIG. 14 and FIG. 15.

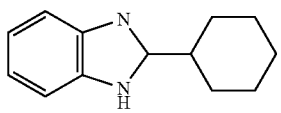 [SMILES: c1ccc2c(c1)NC(C1CCCCC1)N2]

Embodiment 9

Benzaldehyde was prepared by coupling 7-trifluoromethyl-N1,N10-vinyl isoalloxazine chloride as a catalyst for regenerating NAD+ with a horse liver alcohol dehydrogenase to catalyze benzyl alcohol. By using the 7-trifluoromethyl-N1,N10-vinyl isoalloxazine chloride as an oxidizing agent, the generated benzaldehyde reacted with 2-aminobenzenethiol to generate 2-phenylbenzothiazole.

Figure 16:
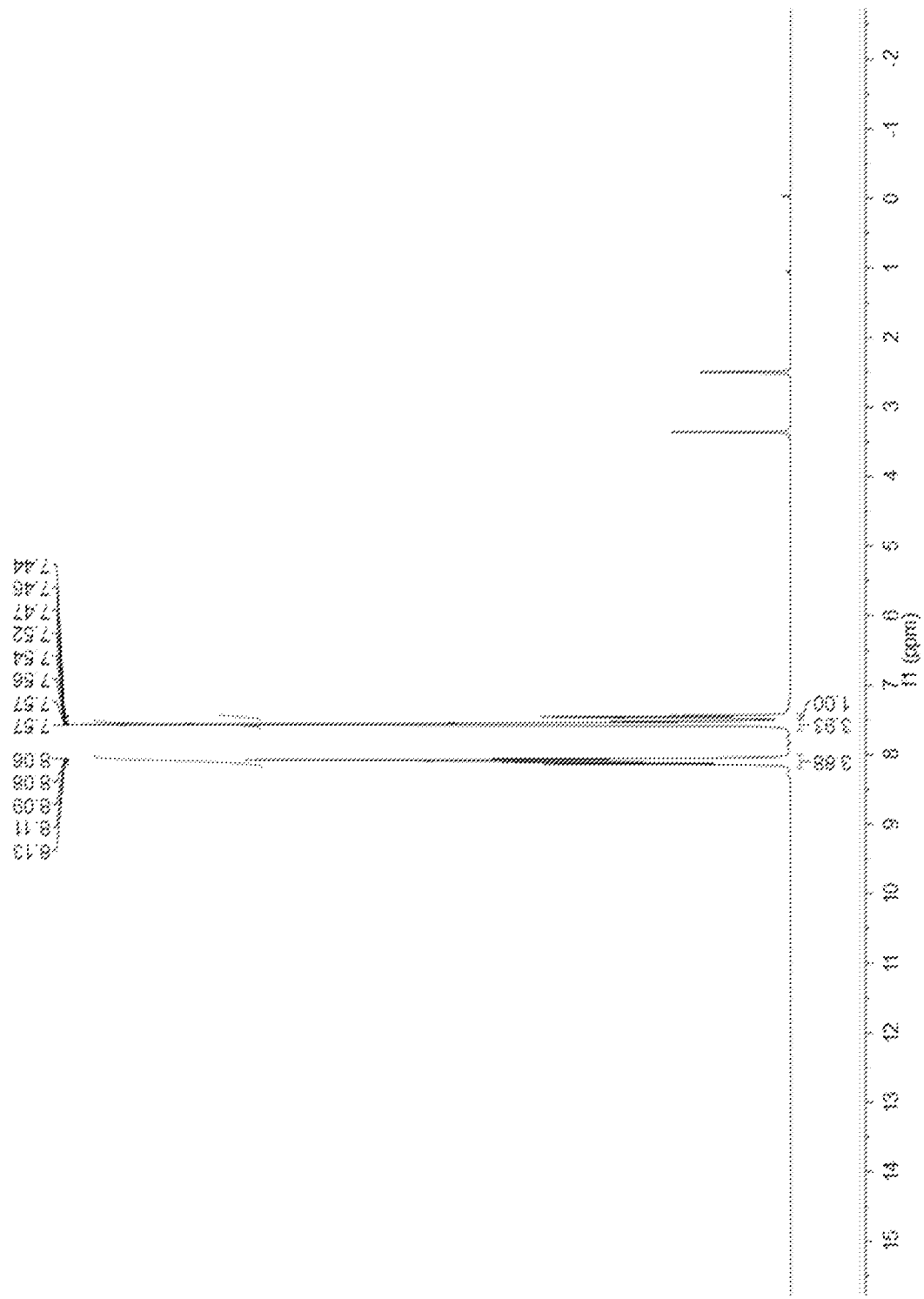
FIG. 16 is a hydrogen spectrum of a product 2-phenylbenzothiazole in Embodiment 9.
Figure 17:
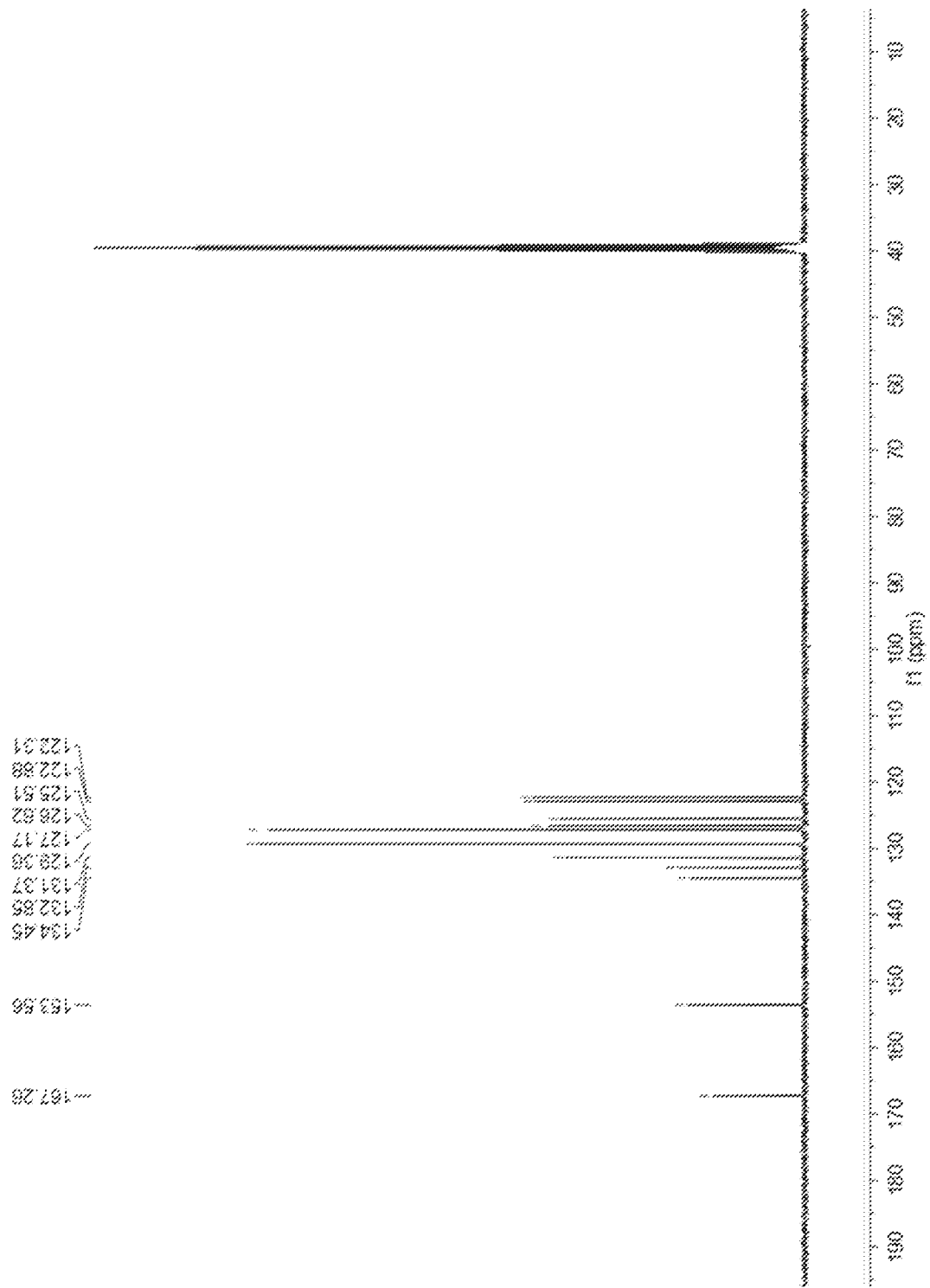
FIG. 17 is a carbon spectrum of the product 2-thienylbenzimidazole in Embodiment 9.

In a shaker at 30° C. and 200 rpm, in 2 mL of 100 mM potassium phosphate buffer with a pH of 7, 5 mM of benzyl alcohol, 1 mM of NAD+, 0.5 mM of 7-trifluoromethyl-N1, N10-vinyl isoalloxazine chloride, 5 U/mL of horse liver alcohol dehydrogenase and 6 mM of o-aminophenol were added, and the reaction solution was communicated with outside air. The reaction lasted for 24 hours. The yield was 18% through quantitative analysis by HPLC. A NMR of the product was shown in FIG. 16 and FIG. 17.

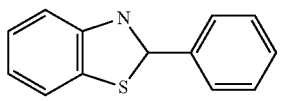 [SMILES: c1ccc(C2Nc3ccccc3S2)cc1]

Embodiment 10

Benzaldehyde was prepared by coupling 7-trifluoromethyl-N1,N10-vinyl isoalloxazine chloride as a catalyst for regenerating NAD+ with a horse liver alcohol dehydrogenase to catalyze benzyl alcohol. By using the 7-trifluoromethyl-N1,N10-vinyl isoalloxazine chloride as an oxidizing agent, the generated benzaldehyde reacted with 2-aminophenol.

In a shaker at 30° C. and 200 rpm, in 2 mL of 100 mM potassium phosphate buffer with a pH of 7, 5 mM of benzyl alcohol, 1 mM of NAD+, 0.5 mM of 7-trifluoromethyl-N1, N10-vinyl isoalloxazine chloride, 5 U/mL of horse liver alcohol dehydrogenase and 6 mM of ortho-aminophenol were added, and the reaction solution was communicated with outside air. The reaction lasted for 24 hours. No 2-phenylbenzoxazole was detected.

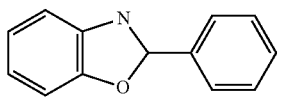 [SMILES: c1ccc(C2Nc3ccccc3O2)cc1]

Embodiment 11

4-nitrobenzaldehyde was prepared by coupling 7-trifluoromethyl-N1,N10-vinyl isoalloxazine chloride as a catalyst for regenerating NAD+ with a horse liver alcohol dehydrogenase to catalyze p-nitrobenzyl alcohol. By using the 7-trifluoromethyl-N1,N10-vinyl isoalloxazine chloride as an oxidizing agent, the generated 4-nitrobenzaldehyde reacted with 1,2-phenylenediamine.

In a shaker at 30° C. and 200 rpm, in 2 mL of 100 mM potassium phosphate buffer with a pH of 7, 5 mM of p-nitrobenzyl alcohol, 1 mM of NAD+, 0.5 mM of 7-trifluoromethyl-N1,N10-vinyl isoalloxazine chloride, 5 U/mL of horse liver alcohol dehydrogenase and 6 mM of 1,2-phenylenediamine were added, and the reaction solution was communicated with outside air. The reaction lasted for 24 hours. The yield was 15% through quantitative analysis by HPLC.

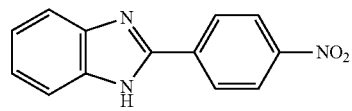

Embodiment 12

Phenyl acetaldehyde was prepared by coupling 7-trifluoromethyl-N1,N10-vinyl isoalloxazine chloride as a catalyst for regenerating NAD+ with a horse liver alcohol dehydrogenase to catalyze phenylethanol. By using the 7-trifluoromethyl-N1,N10-vinyl isoalloxazine chloride as an oxidizing agent, the generated phenyl acetaldehyde reacted with 2-amino-1-butanol.

In a shaker a 30° C. and 200 rpm, in 2 mL of 100 mM potassium phosphate buffer with a pH of 7, 5 mM of phenylethanol, 1 mM of NAD+, 0.5 mM of 7-trifluoromethyl-N1,N10-vinyl isoalloxazine chloride, 5 U/mL of horse liver alcohol dehydrogenase and 6 mM of 2-amino-1-butanol were added, and the reaction solution was communicated with outside air. The reaction lasted for 24 hours. The yield of generated 2-ethyl-5-phenyl-1H-pyrrole was 92% through quantitative analysis by HPLC.

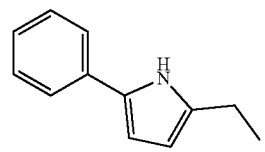

Embodiment 13

Cyclohexanecarboxaldehyde was prepared by coupling 7-trifluoromethyl-N1,N10-vinyl isoalloxazine chloride as a catalyst for regenerating NAD+ with a horse liver alcohol dehydrogenase to catalyze cyclohexanol. By using the 7-trifluoromethyl-N1,N10-vinyl isoalloxazine chloride as an oxidizing agent, the generated cyclohexanecarboxaldehyde reacted with 3-aminopropanol.

In a shaker a 30° C. and 200 rpm, in 2 mL of 100 mM potassium phosphate buffer with a pH of 7, 5 mM of cyclohexanol, 1 mM of NAD+, 0.5 mM of 7-trifluoromethyl-N1,N10-vinyl isoalloxazine chloride, 5 U/mL of horse liver alcohol dehydrogenase and 6 mM of 3-aminopropanol were added, and the reaction solution was communicated with outside air. The reaction lasted for 24 hours. The yield of generated 5,6,7,8-tetrahydroquinoline was 40% through quantitative analysis by HPLC.

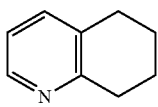

Embodiment 14

Benzenepropanal was prepared by coupling 7-trifluoromethyl-N1,N10-vinyl isoalloxazine chloride as a catalyst for regenerating $NAD^+$ with a horse liver alcohol dehydrogenase to catalyze phenylpropanol. By using the 7-trifluoromethyl-N1,N10-vinyl isoalloxazine chloride as an oxidizing agent, the generated benzenepropanal reacted with 3-amino-methylpropane-1-ol.

In a shaker a 30° C. and 200 rpm, in 2 mL of 100 mM potassium phosphate buffer with a pH of 7, 5 mM of phenylpropanol, 1 mM of $NAD^+$, 0.5 mM of 7-trifluoromethyl-N1,N10-vinyl isoalloxazine chloride, 5 U/mL of horse liver alcohol dehydrogenase and 6 mM of 3-amino-methylpropane-1-ol were added, and the reaction solution was communicated with outside air. The reaction lasted for 24 hours. The yield of generated 3-benzyl-5-benzhydrylpyridine was 50% through quantitative analysis by HPLC.

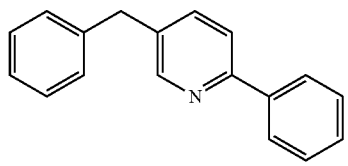 [SMILES: c1ccc(Cc2ccc(-c3ccccc3)nc2)cc1]

Embodiment 15

7-trifluoromethyl-N1,N10-vinyl isoalloxazine chloride used as a catalyst for regenerating $NAD^+$ was coupled with a horse liver alcohol dehydrogenase to catalyze 2-amino-1-propanol, and the 7-trifluoromethyl-N1,N10-vinyl isoalloxazine chloride was used as an oxidizing agent for further oxidation reaction.

In a shaker at 30° C. and 200 rpm, in 2 mL of 100 mM potassium phosphate buffer with a pH of 7, 5 mM of 2-amino-1-propanol, 1 mM of $NAD^+$, 0.5 mM of 7-trifluoromethyl-N1,N10-vinyl isoalloxazine chloride and 5 U/mL of horse liver alcohol dehydrogenase were added, and the reaction solution was communicated with outside air. The reaction lasted for 24 hours. The yield of generated 2,5-dimethyl pyrazine was 45% through quantitative analysis by HPLC.

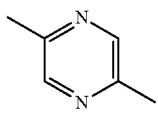

Embodiment 16

4-methoxybenzaldehyde was prepared by coupling 7-trifluoromethyl-N1,N10-vinyl isoalloxazine chloride as a catalyst for regenerating $NAD^+$ with a horse liver alcohol dehydrogenase to catalyze p-methoxybenzyl alcohol. By using the 7-trifluoromethyl-N1,N10-vinyl isoalloxazine chloride as an oxidizing agent, the generated 4-methoxybenzaldehyde reacted with 6-(3,4-diaminophenyl)-5-methyl-4,5-dihydropyridazin-3(2H)-one.

In a shaker a 30° C. and 200 rpm, in 2 mL of 100 mM potassium phosphate buffer with a pH of 7, 5 mM of 4-methoxybenzyl alcohol, 1 mM of $NAD^+$, 0.5 mM of 7-trifluoromethyl-N1,N10-vinyl isoalloxazine chloride, 5 U/mL of horse liver alcohol dehydrogenase and 6 mM of 6-(3,4-diaminophenyl)-5-methyl-4,5-dihydropyridazin-3(2H)-one were added, and the reaction solution was communicated with outside air. The reaction lasted for 24 hours. The yield of generated drug intermediate pimobendan was 50% through quantitative analysis by HPLC.

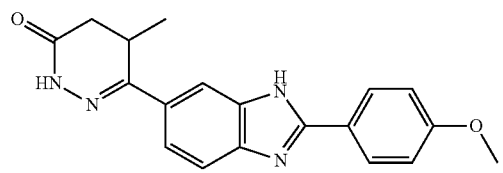 [SMILES: COc1ccc(-c2nc3ccc(C4=NNC(=O)CC4C)cc3[nH]2)cc1]

The present invention provides the idea and the method for preparing the nitrogen-containing heterocyclic compound and the derivative thereof by the enzymatic-chemical cascade method. There are many methods and ways to realize the technical solutions. The above are only the preferred embodiments of the present invention. It should be pointed out that those of ordinary skills in the art can make some improvements and embellishments without departing from the principle of the present invention, and these improvements and embellishments should also be regarded as falling with the scope of protection of the present invention. All the unspecified components in the embodiments can be realized by the prior art.

What is claimed is:

1. A method for preparing a nitrogen-containing heterocyclic compound and a derivative thereof by an enzymatic-chemical cascade method, comprising: reacting an alcohol, an amine, an alcohol dehydrogenase, a flavin molecule and a coenzyme in a solvent to obtain the nitrogen-containing heterocyclic compound and the derivative thereof;

wherein, the nitrogen-containing heterocyclic compound is selected from the group consisting of

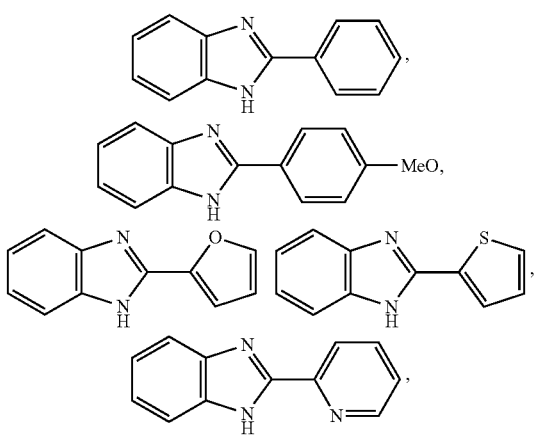

-continued

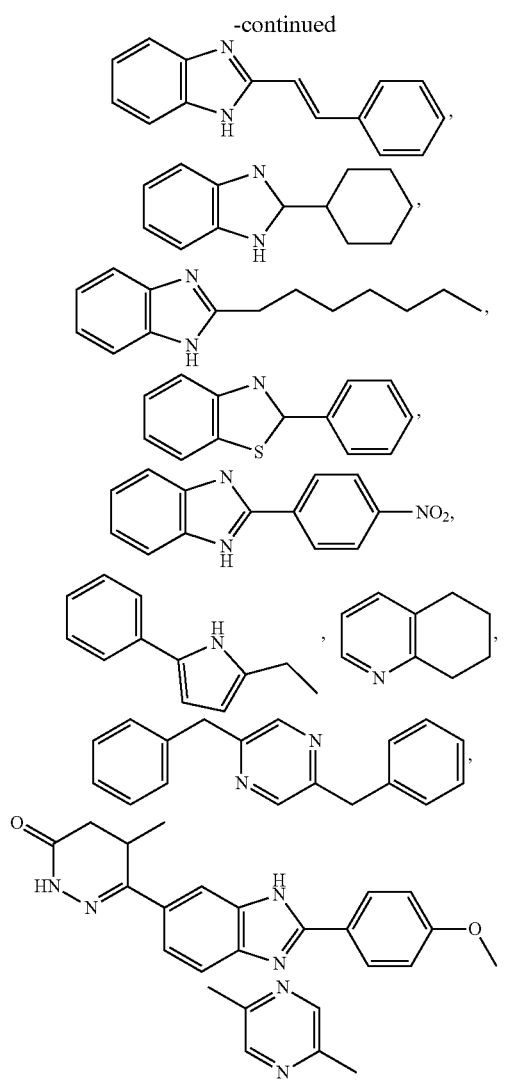

the alcohol is selected from the group consisting of benzyl alcohol, p-methoxybenzyl alcohol, 2-furanmethanol, 2-thiophene methanol, 2-pyridine methanol, n-octanol, benzyl alcohol, p-nitrobenzyl alcohol, cyclohexanol, phenylpropanol, 2-amino-1-propanol, cyclohexyl methanol, cinnamyl alcohol and phenylethanol;

the amine is selected from the group consisting of o-phenylenediamine, o-aminophenol, 2-amino-1-butanol, 2-amino-1-propanol, 3-aminopropanol, 3-amino-2-methylpropane-1-ol and 6-(3,4 diaminophenyl)-4,5 dihydro-5-methyl-3(2H)-phthalazinone;

the coenzyme is any one or a combination of NADP+ and NAD+;

the flavin molecule is any one of the synthetic flavin analog shown in formula I,

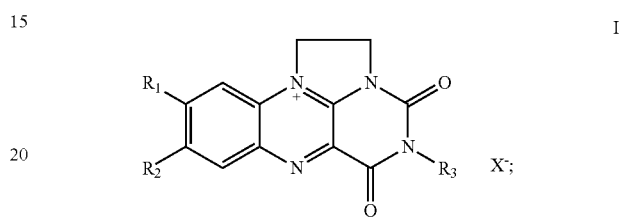

wherein, $R_1$ and $R_2$ are each indendently selected from hydrogen, methyl, trifluoromethyl, methoxy, halogen atom, nitro or amino; $R_3$ is selected from hydrogen, $C_1$-$C_5$ alkyl, phenyl or benzyl; and X- is selected from halide ion, nitrate or trifluoromethanesulfonate.

2. The method according to claim 1, wherein the alcohol dehydrogenase is any one or a combination of ethanol dehydrogenase, horse liver alcohol dehydrogenase, yeast alcohol dehydrogenase and mannitol dehydrogenase.

3. The method according to claim 1, wherein the synthetic flavin analog is any one of 7-trifluoromethyl-N1,N10-vinyl isoalloxazine chloride, 8-chloro-1,10-ethylidene isoalloxazine chloride and 1,10-ethylidene isoalloxazine chloride.

4. The method according to claim 1, wherein the solvent is an aqueous buffer solution.

5. The method according to claim 1, wherein the reaction is performed at a pH of 4 to 10 and 30° C. to 70° C. for 2 hours to 60 hours.

* * * * *